United States Patent
Goldstein et al.

(10) Patent No.: US 7,653,428 B2
(45) Date of Patent: Jan. 26, 2010

(54) METHODS FOR DIAGNOSING A NEURODEGENERATIVE CONDITION

(75) Inventors: Lee E. Goldstein, Marblehead, MA (US); Leo T. Chylack, Jr., Duxbury, MA (US); Ashley Ian Bush, Somerville, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 487 days.

(21) Appl. No.: 11/511,916

(22) Filed: Aug. 28, 2006

(65) Prior Publication Data

US 2007/0038127 A1     Feb. 15, 2007

Related U.S. Application Data

(63) Continuation of application No. 09/935,126, filed on Aug. 21, 2001, now Pat. No. 7,107,092.

(60) Provisional application No. 60/226,590, filed on Aug. 21, 2000.

(51) Int. Cl.
    *A61B 6/00* (2006.01)

(52) U.S. Cl. ............... 600/476; 600/316; 600/318; 600/319; 600/407; 600/477; 424/9.1; 424/9.6; 424/185.1; 351/214; 435/4; 435/6; 435/7.4; 356/300

(58) Field of Classification Search .......... 600/476, 600/407, 477, 316, 318, 319; 800/8, 9, 12; 351/214; 424/9.1, 9.6, 185.1; 435/4, 6, 7.4; 356/300

See application file for complete search history.

(56) References Cited

U.S. PATENT DOCUMENTS

| | | | |
|---|---|---|---|
| 4,529,556 A | 7/1985 | Bruza | 260/465 K |
| 4,836,207 A | 6/1989 | Bursell et al. | 600/318 |
| 4,957,113 A | 9/1990 | Benedek | 128/665 |
| 4,993,827 A | 2/1991 | Benedek | 351/221 |
| 5,171,846 A | 12/1992 | Gupta | 530/400 |
| 5,512,965 A | 4/1996 | Snook | 351/205 |
| 5,540,226 A | 7/1996 | Thurston et al. | 128/633 |
| 5,571,671 A | 11/1996 | Potter | 435/6 |
| 5,784,146 A | 7/1998 | Nanjo et al. | 351/214 |

(Continued)

FOREIGN PATENT DOCUMENTS

CA     2272320     5/1998

(Continued)

OTHER PUBLICATIONS

Ansari and Datiles, "Use of Dynamic Light Scattering and Scheimpflug Imaging for the Early Detection of Cataracts", Diabetes Technol. Ther., 1(2):159-168 (1999).

(Continued)

*Primary Examiner*—Brian Casler
*Assistant Examiner*—Baisakhi Roy
(74) *Attorney, Agent, or Firm*—Mintz Levin Cohn Ferris Glovsky and Popeo, P.C.; Ingrid A. Beattie; Christina Karnakis Stock

(57) ABSTRACT

The invention provides a method of diagnosing, prognosing, staging, and/or monitoring a mammalian amyloidogenic disorder or a predisposition thereto by detecting a protein or polypeptide aggregate in the cortical and/or supranuclear regions of an ocular lens of the mammal.

21 Claims, 8 Drawing Sheets

U.S. PATENT DOCUMENTS

| | | | |
|---|---|---|---|
| 5,837,473 A | 11/1998 | Maggio et al. | 435/7.21 |
| 5,849,340 A | 12/1998 | Hermansson et al. | 425/331 |
| 5,962,463 A | 10/1999 | Nitsch et al. | 514/284 |
| 5,973,779 A | 10/1999 | Ansari et al. | 356/301 |
| 6,001,331 A | 12/1999 | Caprathe et al. | 424/9.1 |
| 6,013,034 A | 1/2000 | Fernandes Da Cunha Vaz et al. | 600/476 |
| 6,054,114 A | 4/2000 | Lansbury, Jr. et al. | 424/1.11 |
| 6,096,510 A | 8/2000 | Hochman | 435/29 |
| 6,107,050 A | 8/2000 | Alkon et al. | 435/7.4 |
| 6,114,175 A | 9/2000 | Klunk et al. | 436/63 |
| 6,133,259 A | 10/2000 | Klunk et al. | 514/230.5 |
| 6,153,171 A | 11/2000 | Rowe et al. | 424/9.1 |
| 6,168,776 B1 | 1/2001 | Klunk et al. | 424/1.11 |
| 6,198,532 B1 | 3/2001 | Cabib et al. | 356/346 |
| 6,329,531 B1 | 12/2001 | Turner et al. | 548/455 |
| 6,423,270 B1 | 7/2002 | Wall | 422/61 |
| 6,600,017 B1 | 7/2003 | Glabe et al. | 530/345 |
| 6,818,218 B2 | 11/2004 | Schenk | 424/185.1 |
| 6,849,249 B2 * | 2/2005 | Goldstein et al. | 424/9.1 |
| 7,107,092 B2 * | 9/2006 | Goldstein et al. | 600/476 |
| 7,297,326 B2 * | 11/2007 | Goldstein et al. | 424/9.1 |
| 2002/0091321 A1 | 7/2002 | Goldstein et al. | 600/476 |
| 2002/0098153 A1 | 7/2002 | Allen et al. | 424/9.364 |
| 2002/0133019 A1 | 9/2002 | Klunk et al. | 548/156 |
| 2002/0187157 A1 | 12/2002 | Jensen et al. | 424/185.1 |
| 2003/0149997 A1 | 8/2003 | Hageman | 800/8 |

FOREIGN PATENT DOCUMENTS

| | | |
|---|---|---|
| CA | 2301142 | 2/1999 |
| EP | 0 459 454 B1 | 12/1991 |
| WO | WO 98/22146 | 5/1998 |
| WO | WO 99/08695 | 2/1999 |
| WO | WO 99/24394 | 5/1999 |
| WO | WO 01/50134 A2 | 7/2001 |

OTHER PUBLICATIONS

Ansari et al., "A fiber optic probe for monitoring protein aggregation, nucleation and crystallization", *J. Crystal Growth*, 168:216-226 (1996).

Atwood et al., "Dramatic aggregation of Alzheimer Aβ by Cu(II) is induced by Conditions representing physiological acidosis", *J. Biol. Chem.*, 273(21):12817-12826 (1998).

Benedek et al., "Quantitative detection of the molecular changes associated with early cataractogenesis in the living human lens using quasielastic light scattering", *Curr. Eye Res.*, 6(12):1421-1432 (1987).

Berk et al., "Ocular findings in 55 patients with Down's syndrome", *Ophthalmic Genetics* 17(1):15-19 (1996).

Blacker and Tanzi, "The genetics of Alzheimer disease", *Arch. Neurol.*, 55:294-296 (1998).

Bloemendal, H., "Disorganization of membranes and abnormal intermediate filament assembly lead to cataract", *Invest. Ophthalmol Vis. Sci.*, 32(3):445-455 (1991).

Borchelt et al., "Familial Alzheimer's disease-linked presenilin 1 variants elevate Aβ1-42/1-40 ratio in vitro and in vivo", *Neuron*, 17:1005-1013 (1996).

Brás et al., "Oxidative stress in trisomy 21", *Ophthalmic Paediatrics and Genetics*, 10(4):271-277 (1989).

Bron et al., The ageing lens *Ophthalmologica*, 214:86-104 (2000).

Bush, A.I., "Metals and neuroscience", Curr. Opin. Chem. Biol., 4:184-191 (2000).

Cai et al., "Release of excess amyloid βprotein precursor", *Science*, 259:514-516 (1993).

Chartier-Harlin et al., "Early-onset Alzheimer's disease caused by mutations at codon 717 of the β-amyloid precursor protein gene", *Nature*, 353:884 (1991).

Chylack et al., "Classification of human senile cataractous change by the American Cooperative Cataract Research Group method", *Invest. Optham. Vis. Sci.*, 24:424-431 (1983).

Citron et al., "Mutation of the β-amyloid precursor protein in familial Alzheimer's disease increases β-protein production", Nature, 360:672-674 (1992).

Cuajungco et al., "Evidence that the β-amyloid plaques of Alzheimer's disease represent the redox-silencing and entombment of aβ by zinc", *J. Biol. Chem.*, 275:19439-19442 (2000).

da Cunha and Moreira, "Ocular findings in Down's syndrome", *Am. J. Ophthalmol.*, 122:236-244 (1996).

Duff et al., "Increased amyloid-β42(43) in brains of mice expressing mutant presenilin 1", *Nature*, 383:710-713 (1996).

Ernst and Hay, "The US economic social costs of Alzheimer's disease revisited", *Am. J. Pub. Health*, 84(8):1261-1264 (1994).

Esch et al., "Cleavage of amyloid β peptide during constitutive processing of its precursor", *Science*, 248:1122-1124 (1990).

Frederikse and Zigler Jr., "Presenilin expression in the ocular lens", *Curr. Eye Res.*, 17:947-952 (1998).

Frederikse et al., "Alternatively spliced Alzheimer, precursor, protein mRNAs and proteins in lenses", *Invest. Ophthalmol. Vis. Sci.*, 41(4):S627, Abstract No. 3330-B428 (2000).

Frederikse et al., "Oxidative stress increases production of β-amyloid precursor protein and β-amyloid (Aβ) in mammalian lenses, and Aβ has toxic effects on lens epithelial cells", *J. Biol. Chem.*, 271(17):10169-10174 (1996).

Glenner & Wong, "Alzheimer's disease: initial report of the purification and characterization of a novel cerebrovascular amyloid protein", *Biochem. Biophys. Rev. Commun.*, 120(3): 885-890 (1984).

Goate et al., "Segregation of a missense mutation in the amyloid precursor protein gene with familial Alzheimer's disease", *Nature*, 349:704-706 (1991).

Goldgaber et al., "Characterization and chromosomal localization of a cDNA encoding brain amyloid of Alzheimer's disease ", *Science*, 235:877-880 (1987).

Haass et al., "Amyloid β-peptide is produced by cultured cells during normal metabolism", *Nature*, 359:322-325 (1992).

Hankinson, S. E., "The Epidemiology of Age-Related Cataract" in *Principles and Practice of Ophthalmology*, D. M. Albert and F. A. Jakobiec, editors, Philadelphia, PA, W. B. Saunders, Co., Chapter 108, pp. 1255-1265 (1994).

Hanlon et al., "Prospects for in vivo raman spectroscopy", *Phys. Med. Biol.*, 45:R1-R59 (2000).

Harding, J. J., "Alzheimer disease and cataract: common threads", *Alzheimer Dis. Assoc. Disorders*, 11(3):123 (1997).

Harding, J. J., "Cataract, Alzheimer's disease, and other conformational diseases", *Curr. Opin. Ophthalmol.*, 9:10-13 (1998).

Hendricks et al., "Presenile dementia and cerebral haemorrhage linked to a mutation at codon 692 of the β-amyloid precursor protein gene", *Nat. Genet.*, 1:218-221 (1992).

Hendrie, H. C., "Epidemiology of dementia and Alzheimer's disease ", *Am. J. Geriatric Psychiatry*, 6(2 Suppl 1): S3-S18 (1998).

Hsiao et al., "Correlative memory deficits, Aβ elevation, and amyloid plaques in transgenic mice", *Science*, 274:99-102 (1996).

Huang et al., "The Aβ peptide of Alzheimer's disease directly produces hydrogen peroxide through metal ion reduction", *Biochemistry*, 38(24):7609-7616 (1999).

Huang et al., "Zinc-induced Alzheimer's Aβ1-40 aggregation is mediated by conformational factors", *J. Biol. Chem.*, 272(42):26464-26470 (1997).

Huang et al., "Cu(II) potentiation of Alzheimer Aβ neurotoxicity", *J. Biol. Chem.*, 274(52):37111-37116 (1999).

Huang et al., Alzheimer's disease, β-amyloid protein and zinc, *J. Nutr.*, 130 (5 Suppl):1488S-1492S (2000).

Kang et al., "The precursor al Alzheimer's disease amyloid A4 protein resembles a cell-surface receptor", *Nature*, 325:733-736 (1987).

Leske et al., "Antioxidant vitamins and nuclear opacities", *Ophthalmology*, 105: 831-836 (1998).

Levy et al., "Mutation of the Alzheimer's disease amyloid gene in hereditary cerebral hemorrhage, Dutch type", *Science*, 248:1124-1126(1990).

Libondi et al., "In vivo measurement of the aging rabbit lens using quasielastic light scattering", *Curr. Eye Res.*, 5(6):411-419 (1986).

Lott, I.T., "Down's syndrome, aging, and Alzheimer's disease : a clinical review", *Ann. NY Acad. Sci.*, 396:15-27 (1982).

Lott, I. T., "The neurology of Alzheimer disease in Down syndrome", *Prog. Clin. Biol. Res.*, 379:1-14 (1992).

Lovell et al., "Copper, iron and zinc in Alzheimer's disease senile plaques", *J.Neurol. Sci.*, 158:47-52 (1998).

Markesbery and Ehmann, "Oxidative Stress in Alzheimer's Disease" in Alzheimer Disease, R. D. Terry, R. Katzman, K.L. Bick and S.S. Sisodia, editors, New York, Libbincott Williams and Wilkins, Chapter 27, pp. 401-414 (1999).

Masters et al., "Amyloid plaque core protein in Alzheimer disease and Down syndrome", *Proc. Natl. Acad. Sci. USA*, 82:4254-4249 (1985).

Masters et al., "Neuronal origin of a cerebral amyloid: neurofibrillary tangles of Alzheimer's disease contain the same protein as the amyloid of plaque cores and blood vessels", *EMBO J.*, 4(11):2757-2763 (1985).

Miura et al., "Raman spectroscopic study on the copper(II) binding mode of prion octapeptide and its pH dependence", *Biochemistry*, 38:11560-11569 (1999).

Miura et al., "Metal binding modes of Alzheimer's amyloid $\beta$-peptide in insoluble aggregates and soluble complexes", *Biochemistry*, 39:7024-7031(2000).

Mullan et al., "A pathogenic mutation for probable Alzheimer's disease in the APP gene at the N-terminus of $\beta$-amyloid", *Nat. Genet.*, 1:345 (1992).

Murrell et al., "A mutation in the amyloid precursor protein associated with hereditary Alzheimer's disease", *Science*, 254:97-99 (1991).

Oyama et al., "Down's syndrome: up-regulation of $\beta$-amyloid protein precursor and $\tau$ mRNAs and their defective coordination", *J. Neurochem.*, 62:1062-1066 (1994).

Pappolla et al., "Evidence of oxidative stress and in vivo neurotoxicity of $\beta$-amyloid in a transgenic mouse model of Alzheimer's disease", *Am. J. Pathol.*, 152(4):871-877 (1998).

Pueschel, S. M., "Clinical aspects of Down syndrome from infancy to adulthood", *Am. J. Med. Genet.*, 7(Suppl.):52-56 (1990).

Robakis et al., "Molecular cloning and characterization of cDNA encoding the cerebrovascular and the neuritic plaque amyloid peptides", *Proc. Natl. Acad. Sci. USA*, 84:4190-4194 (1987).

Roher et al., "Morphological and biochemical analyses of amyloid plaque core proteins purified from Alzheimer's disease brain tissue", *J. Neurochem.*, 61:1916-1926 (1993).

Sano et al., "A controlled trial of selegiline, alpha-tocopherol, or both as treatment for Alzheimer's disease", *N. Engl. J. Med.*, 336:1216-1222 (1997).

Scheuner et al., "Secreted amyloid ($\beta$-protein similar to that in the senile plaques of Alzheimer's disease is increased in vivo by the presenilin 1 and 2 and APP mutations linked to familial Alzheimer's disease", *Nat. Med.*, 2(8):864-70 (1996).

Seubert et al., "Isolation and quantification of soluble Alzheimer's $\beta$-peptide from biological fluids", *Nature*, 359:325-327 (1992).

Shoji et al., "Production of the Alzheimer amyloid $\beta$ protein by normal proteolytic processing", *Science*, 258: 126-129 (1992).

Smith et al., "Amyloid-$\beta$ deposition in Alzheimer transgenic mice is associated with oxidative stress", *J. Neurochem.*, 70:2212-2215 (1998).

Spector, A., "Oxidative stress-induced cataract: mechanism of action", *FASEB J.*, 9:1173-1182 (1995).

St. George-Hyslop, P. H., "Molecular Genetics of Alzheimer's Disease", *Biol. Psychiatry*, 47:183-199 (2000).

Stark et al., "Changing trends in intraocular lens implantation", *Arch. Ophthalmol.*, 107:1441-1444 (1989).

Suzuki et al., "An increased percentage of long amyloid $\beta$ protein secreted by familial amyloid $\beta$ protein precursor ($\beta APP_{717}$) mutants", *Science*, 264:1336-1340 (1994).

Suzuki et al., "Inhibitory effect of copper(II) on zinc(II)-induced aggregation of amyloid $\beta$-peptide", *Biochem. Biophys. Res. Commun.*, 285:991-996 (2001).

Tanzi et al., "Amyloid $\beta$ protein gene: cDNA, mRNA distribution, and genetic linkage near the Alzheimer locus", *Science*, 235:880-884 (1987).

Tomski & Murphy, "Kinetics of aggregation of synthetic $\beta$-amyloid peptide", *Arch. Biochem. Biophys.*, 294(2):630-638 (1992).

Vigo-Pelfrey et al., "Characterization of $\beta$-amyloid peptide from human cerebrospinal fluid", *J. Neurochem.*, 61:1965-1968 (1993).

Whitehouse et al., "Molecular Biology of Alzheimer's Disease", *Mol. Genet. Med.*, Chapter 4, 3:95-137 (1993).

Yankner et al., "Neurotrophic and neurotoxic effects of amyloid $\beta$ protein: reversal by Tachykinin neuropeptides", *Science*, 250:279-282 (1990).

Frederikse et al., "Prion protein expression in mammalian lenses", *Curr. Eye Res.*, 20(2):137-143 (2000).

Goldstein et al., "A$\beta$ peptides in human and amyloid-bearing transgenic mouse lens: Implications for Alzheimer's disease and cataracts", *IOVS*, Abstract #1614, 42(4):S299 (2001).

Klunk et al., "Chrysamine-G Binding to Alzheimer and Control Brain: Autopsy Study of a New Amyloid Probe", *Neurobiol. Aging*, 16(4):541-548 (1995).

LeVine, III, H., "Thioflavine T interaction with synthetic Alzheimer's disease $\beta$-amyloid peptides: Detection of amyloid aggregation in solution", *Protein Sci.*, 2:404-410 (1993).

Bacskai et al., "Imaging Amyloid-$\beta$ Deposits In Vivo", *J. Cereb. Blood Flow Metabol.*, 22(9):1035-1041 (2002).

Brown et al., "The Hyperlipoproteinemias and Other Disorders of Lipid Metabolism", in *Harrison's Principles of Internal Medicine Twelfth Edition*, Chapter 326, pp. 1814-1815, McGraw-Hill, Inc. (1991).

Burggren et al., "Structural and Functional Neuroimaging in Alzheimer's Disease: An Update", *Curr. Top. Medic. Chem.*, 2(4):385-393 (2002).

Christie et al., "Growth Arrest of Individual Senile Plaques in a Model of Alzheimer's Disease Observed by In Vivo Multiphoton Microscopy", *J. Neurosci.*, 21(3):858-864 (2001).

Frederikse, P.H., "Amyloid-like protein structure in mammalian oculars lenses", *Curr. Eye Res.*, 20(6):462-468 (2000).

Frederikse et al., "Oxidative Stress Increases Production of $\beta$-Amyloid Precursor Protein and $\beta$-Amyloid (A$\beta$) in Mammalian Lenses, and A$\beta$ Has Toxic Effects on Lens Epithelial Cells", *J. Biol. Chem.*, 271(17):10169-10174 (1996).

Helmuth, L., "Long-Awaited Technique Spots Alzheimer's Toxin", *Science*, 297:752-753 (2002).

Kauffman et al., "Clioquinol (Iodochlorhydroxyquin, Vioform) and Iodoquniol (Diiodohydroxyquin): Blindness and Neuropathy", *Pediatrics*, 86(5):797-798 (1990).

Klunk et al., "Imaging A$\beta$ Plaques in Living Transgenic Mice with Mulitphoton Microscopy and Methoxy-X04, a Systemically Administered Congo Red Derivative", *J. Neuropathol. Exp. Neurol.*, 61(9):797-805 (2002).

Klunk et al., "The Binding of 2-(4'-Methylaminophenyl) Benzothiazole to Postmortem Brain Homogenates Is Dominated by the Amyloid Component", *J. Neurosci.*, 23(6):2086-2092 (2003).

Klunk et al., "Uncharged thioflavin-T derivatives bind to amyloid-beta protein with high affinity and readily enter the brain", *Life Sci.*, 69:1471-1484 (2001).

Klunk et al., "Development of Small Molecule Probes for the Beta-Amyloid Protein of Alzheimer's Disease" *Neurobiol. Aging*, 15(6):691-698 (1994).

Kung et al., "IMPY: an improved thioflavin-T derivative for the in vivo labeling of $\beta$-amyloid plaques", *Brain Res*, 956:202-210 (2002).

Kung et al., "Radioiodinated Styrylbenzene Derivatives as Potential SPECT Imaging Agents for Amyloid Plaque Detection in Alzheimer's Disease", *J. Mol Neurosci.*, 19(1/2):7-10 (2002).

Lee et al., "Isomerizetion of(Z,Z) to (E,E)1-Bromo-2,5-bis-(3-hydroxycarbonyl-4-hydroxy)-styrylbenzene in Strong Base: Probes for Amyloid Plaques in the Brain", *J. Med. Chem.*, 44:2270-2275 (2001).

Lewis, R., "Imaging Early Alzheimer Disease", *The Scientist*, 16(21): (2002).

Link et al., "Visualization of fibrillar amyloid deposits in living, transgenic *Caenorhabditis elegans* animals using the sensitive amyloid dye, X-34", *Neurobiol. Aging*, 22(2):217-226 (2001).

Martinez-Senac et al., "Structure of Alzheimer $\beta$-amyloid peptide (25-35) and its interaction with negatively charged phospholipid vesicles", *Eur. J. Biochem.*, 265:744-753 (1999).

Mathis et al., "A Lipophilic Thioflavin_T Derivative for Positron Emission Tomography (PET) Imaging of Amyloid in Brain", *Biorganic Medic. Chem. Lett.*, 12:295-298 (2002).

McLellan et al., "In Vivo Imaging of Reactive Oxygen Species Specifically Associated with Thoiflavine S-Positive Amyloid Plaques by Multiphoton Microscopy", *J. Neurosci.*, 23(6):2212-2217 (2003).

Pettergrew et al., "Clinical and Neurochemical Effects of Acetyl-L-Carnitine in Alzheimer's Disease", *Neurobiol. Aging*, 16(1):1-4 (1995).

Selkoe, D., "Toward a Comprehensive Thoery for Alzheimer's Disease, Hypothesis: Alzheimer's Disease Is Caused by the Cerebral Accumulation and Cytotoxicity of Amyloid β-Protein", *Annal. N.Y. Acad. Sci.*, 924:17-25 (2000).

Siik et al., "Lens autofluorescence and light scatter in relation to the lens opacities classification system, LOCS III", *Acta Ophthamol. (Scand.)*, 77(5):509-514 (1999).

Siik et al., "Lens autofluorescence in healthy individuals", *Acta Ophtamol. (Copenh)*, 69(2):187-192 (1991).

Siik et al, "Influence of lens autofluorescence on retinal nerve fiber layer evaluation", *Acta Ophthamol. (Scand.)*, 75(5):524-527 (1997).

Siik et al., "Autoflourescence in cataractous human lens and its relationship to light scatter", *Acta Ophthamol. (Copenh)*, 70(3):383-388 (1992).

Siik et al., "Light scatter in aging and cataractous human lens", *Acta Ophthamol. (Cophenh)*, 70(3):383-388 (1993).

Skovronsky et al., "In vivo detection of amyloid plaques in a mouse model of Alzheimer's disease", *Proc. Natl. Acad. Sci. U.S.A.*, 97(13):7609-7614, 2000.

Styren et al., "X-34, A Fluorescent Derivative of Congo Red: A Novel Histochemical Stain for Alzheimer's Disease Pathology", *J. Histochem. Cytochem.*, 48(9):1223-1232 (2000).

Wilson et al., eds., Harrison's Principles of Internal Medicine, 12th Edition, pp. 1814-1815 (1991).

* cited by examiner

METHODS FOR DIAGNOSING A NEURODEGENERATIVE CONDITION

RELATED APPLICATIONS

This application is a continuation application of U.S. Ser. No. 09/935,126, filed Aug. 21, 2001 now U.S. Pat. No. 7,107,092, which claims priority to U.S. provisional application 60/226,590, filed Aug. 21, 2000, the entire contents of which are hereby incorporated by reference.

BACKGROUND OF THE INVENTION

The invention relates to the diagnosis of neurodegenerative conditions.

Alzheimer's Disease (AD) is a major public health concern for the aging population and the third most expensive illness in the United States, behind heart disease and cancer. Approximately 4 million Americans have AD. The prevalence of the disease in persons over 65 years of age is one in ten and increases to nearly half in those over 85. The cost of AD care is estimated at over $100 billion dollars per annum. AD is presently incurable and the causes remain uncertain. Scientists working to determine the cause and pathology of AD have identified various contributing factors. It is believed that cerebral accumulation and toxicity of the β-amyloid protein (Aβ) as are causative events in AD pathology. The determinative method of diagnosis of AD remains the postmortem detection of cerebral plaques by autopsy. Antemortem diagnosis of the disease is limited to clinical techniques with poor reproducibility, specificity, and sensitivity. Currently, there are no means to detect the AD disease process prior to the emergence of clinical signs and symptoms of the disease.

SUMMARY OF THE INVENTION

The invention features a non-invasive antemortem test to aid in the diagnosis, prognosis, staging, and monitoring of a neurodegenerative condition such as AD. Dynamic light scattering (DLS; a.k.a. quasi-elastic light scattering (QLS)), Raman spectroscopy, and other optical instrumentation allow detection of morphological changes in the eye, which are associated with AD.

A method of diagnosing, prognosing, staging, and/or monitoring a mammalian amyloidogenic disorder or a predisposition thereto is carried out by detecting a protein or polypeptide aggregate in the cortical and/or supranuclear region of an ocular lens of the mammal. This determination is compared to or normalized against the same determinations in the nuclear region of the same lens where more general effects of aging are observed. Comparisons are also made to a population norm, e.g., data compiled from a pool of subjects with and without disease. The presence of or an increase in the amount of aggregate in the supranuclear and/or cortical lens regions of the test mammal compared to a normal control value indicates that the test mammal is suffering from, or is at risk of, developing an amyloidogenic disorder. A normal control value corresponds to a value derived from testing an age-matched individual known to not have an amyloidogenic disorder or a value derived from a pool of normal, healthy (non-AD) individuals. An amyloidogenic disorder is one that is characterized by deposition or accumulation of an amyloid protein or fragment thereof in the brain of an individual. Amyloidogenic disorders include AD, Familial AD, Sporadic AD, Creutzfeld-Jakob disease, variant Creutzfeld-Jakob disease, spongiform encephalopathies, Prion diseases (including scrapie, bovine spongiform encephalopathy, and other veterinary prionopathies), Parkinson's disease, Huntington's disease (and trinucleotide repeat diseases), amyotrophic lateral sclerosis, Down's Syndrome (Trisomy 21), Pick's Disease (Frontotemporal Dementia), Lewy Body Disease, neurodegeneration with brain iron accumulation (Hallervorden-Spatz Disease), synucleinopathies (including Parkinson's disease, multiple system atrophy, dementia with Lewy Bodies, and others), neuronal intranuclear inclusion disease, tauopathies (including progressive supranuclear palsy, Pick's disease, corticobasal degeneration, hereditary frontotemporal dementia (with or without Parkinsonism), and Guam amyotrophic lateral sclerosis/parkinsonism dementia complex). These disorders may occur alone or in various combinations. For example, individuals with AD are characterized by extensive accumulation of amyloid in the brain in the form of senile plaques, which contain a core of amyloid fibrils surrounded by dystrophic neurites. Some of these patients exhibit clinical signs and symptoms, as well as neuropathological hallmarks, of Lewy Body disease.

The presence and/or an increase in the amount of an amyloid protein or polypeptide detected in a subject's eye tissue over time indicates a poor prognosis for disease, whereas absence or a decrease over time indicates a more favorable prognosis. For example, a decrease or decrease in the rate of accumulation in amyloid protein or similar changes in the associated ocular morphological features in eye tissue after therapeutic intervention indicates that the therapy has clinical benefit. Therapeutic intervention includes drug therapy such as administration of a secretase inhibitor, vaccine, antioxidant, anti-inflammatory, metal chelator, or hormone replacement or non-drug therapies.

Mammals to be tested include human patients, companion animals such as dogs and cats, and livestock such as cows, sheep, pigs horses and others. For example, the methods are useful to non-invasively detect bovine spongiform encephalopathy (mad cow disease), scrapie (sheep), and other prionopathies of veterinary interest]

For example, the diagnostic test is administered to a human who has a positive family history of familial AD or other risks factors for AD (such as advanced age), or is suspected of suffering from an amyloidogenic disorder, e.g., by exhibiting impaired cognitive function, or is at risk of developing such a disorder. Subjects at risk of developing such a disorder include elderly patients, those who exhibit dementia or other disorders of thought or intellect, or patients with a genetic risk factor.

A disease state is indicated by the presence of amyloid protein aggregates or deposits in the supranuclear or cortical region of a mammalian lens. For example, the amount of amyloid protein aggregates is increased in a disease state compared to a normal control amount, i.e., an amount associated with a non-diseased individual. Amyloid proteins include β-amyloid precursor protein (APP), Aβ, or a fragment thereof (e.g., $A\beta_{1-42}$) as well as prion proteins, and synuclein. Protein or polypeptide aggregates may contain other proteins in addition to Aβ (such as α-, β-, and/or γ-crystallin). Unlike amyloid protein deposition in brain tissue which is primarily extracellular, ocular deposition in lens cortical fiber cells is cytosolic.

Aggregates are detected non-invasively, i.e., using a device or apparatus that is not required to physically contact ocular tissue. For example, the invention includes a method of diagnosing an amyloidogenic disorder or a predisposition thereto in a mammal, by illuminating mammalian lens tissue with an excitation light beam and detecting scattered or other light signals emitted from the tissue. Aggregates are detected with quasi-elastic light scattering techniques (a.k.a. dynamic light scattering), Raman spectroscopy, fluorimetry, and/or other methods of analyzing light returned from the test tissue. An increase of scattered light emitted from the cortical and/or supranuclear regions of an ocular lens indicates that the mammal is suffering from, or is at risk of developing an amyloidogenic disorder such as AD. Excitation light is in the range of 350-850 nm. Preferably, the excitation light beam is a low wattage laser light such as one with a wavelength of 450-550 nm. Alternatively, the excitation light beam is in the very near-UV (392-400 nm) or visible (400-700 nm) range.

The invention also encompasses a method of monitoring the efficacy of a therapeutic agent or intervention for disease or amyloidogenic disorder by detecting polypeptide aggregates over time, e.g., before therapy begins and at various times after (or during) therapeutic intervention. An increase in the amount or rate of accumulation of aggregates indicates a less favorable prognosis or less favorable response to therapy, whereas a decrease in the amount or rate indicates a favorable response to therapy or a favorable prognosis. For example, a pre-treatment status of the patient is determined, the patient is treated, and then the patient's condition is followed using QLS, Raman techniques, or fluorimetry. An increase in the amount or rate of formation of aggregate or accumulation of amyloidogenic protein or peptides is compared to a normal control value or a prior measurement in the same individual mammal.

Detection of protein aggregation or accumulation or deposition of amyloidogenic proteins or peptides in the supranuclear/cortical region of an ocular lens is ratiometrically, volumetrically, or otherwise mathematically compared to the same or similar measurements in the nuclear or other regions of the lens. The methods are useful to measure protein aggregation or accumulation or deposition of amyloidogenic proteins or peptides in other ocular tissues, including but not limited to the cornea, the aqueous humor, the vitreous humor, and the retina.

A significant advantage of the methods described herein is the ability to reliably and non-invasively diagnose AD antemortem. Prior to the invention, no reliable antemortem diagnostic methods were available. Based on the discovery that an increase in Aβ is detectable human AD patient lenses compared to normal human lenses, early detection of neurodegeneration is possible. Thus, another advantage of the method is detection of a pathologic state (or pre-pathologic state) prior to any clinical indication of disease, e.g., impaired cognition.

Yet another advantage is the specificity of the diagnostic method. Aggregation in a distinct anatomical region of the lens, i.e., supranuclear and/or cortical region, rather than the nuclear region of the lens indicates a disease state. Neuropathologically confirmed human AD is associated with a relatively uncommon cataract phenotype (the supranuclear/deep cortical cataract). This supranuclear/cortical cataract is distinct from the much more common age-related cataract, which is found in the lens nucleus. Aβ in the lens of human AD patients was found to be associated with intracellular cytoplasmic aggregated lens particles, which are large enough to scatter light and are evident in the same region of the lens in which the supranuclear/cortical cataract is observed. This same type of cataract occurs in a transgenic mouse model of AD (APP2576) which overexpresses human Aβ species.

The QLS technique is used to non-invasively detect and quantitate lens protein aggregation in this animal model of AD and in human subjects. An additional advantage to this technique is the ability to monitor disease progression as well as responsiveness to therapeutic intervention. Aβ-associated lens aggregates are found exclusively in the cytoplasmic intracellular compartment of human lens cells, specifically lens cortical fiber cells in contrast to Aβ deposits in the brain, which are largely extracellular. Aβ fosters human lens protein to aggregate through metalloprotein redox reactions and this aggregation by chelation or antioxidant scavengers.

Aβ and αB-crystallin crosslink not only in the lens, but also in the brain. Finally, an important advantage of the method is that the amount and rate of progression of Aβ aggregation and/or crosslinking in the eye closely parallels disease progression in the brain, providing an accurate and reliable determination of pathology in an otherwise inaccessible tissue.

Other features and advantages of the invention will be apparent from the following description of the preferred embodiments thereof, and from the claims.

BRIEF DESCRIPTION OF THE FIGURES

FIG. 1a shows a stereoscopic slit-lamp photomicrographic image of one lens from donor #323 (79 y.o. female). Convergence of white dots beneath images indicates stereoscopy. Supranuclear cataract is apparent in the left-hand superior quadrant. FIG. 1b shows the same lens as in FIG. 1a. In FIG. 1b, supranuclear opacification is indicated with a white dashed arc, and patchy supranuclear opacities are indicated with a white arrowhead. Nuclear opacification (black arrowhead) and nuclear brunescence (yellow dashed circle) are typical of age-related nuclear cataracts, which were co-morbidly present in this patient. FIG. 1c shows a lens from donor #283 (82 y.o. female). Prominent circumferential supranuclear opacification is evident (dashed white circle). Some axial posterior subcapsular cataract is also present. Black box indicates region from which ultra-thin cyrosections were obtained for anti-Aβ immunogold electron microscopy (IEM). Absence of nuclear opacification. FIG. 1d shows a lens from donor #681 (68 y.o. female). Equatorial and supranuclear opacification are present (dashed white arc). Absence of nuclear opacification. FIG. 1e shows a lens from donor #301 (75 y.o. female). Patchy circumferential supranuclear opacification is present (dashed white circle). Small areas of cortical opacification are also present. Absence of nuclear opacification. FIG. 1f shows a control lens from donor #1473 (44 y.o. male without Alzheimer's disease neuropathology). Evidence of supranuclear or age-related nuclear cataracts is absent. FIG. 1g shows a slit-lamp photomicrograph of a whole lens from a 10-month old APP2576 transgenic mouse overexpressing human Aβ. A dense hypermature cataract (white arrowhead) occupies the entire cortical region. A deeper supranuclear cataract (black arrowhead) surrounds a clear lens nucleus. FIG. 1h shows a photomicrographic image of anti-Aβ IEM of the cortical region of human lens from donor #283. The anti-Aβ mAb 4G8 directed against the intramembranous APP domain ($A\beta_{17-24}$) was used to probe for Aβ immunoreactivity. Scale bar=200 nm. FIG. 1i shows a greater magnification of the immunogold particle clusters. Scale bar=500 nm. FIG. 1j shows a control section of the same cortical region incubated with control rabbit IgG as the primary antibody. FIG. 1k shows a photomicrographic image of anti-Aβ (4G8) IEM of the cortical region of human lens from a normal 14 y.o. male FIG. 2a shows a conventional photograph of a lens ex vivo and FIG. 2b shows a slit lamp photograph of the same lens. The cataract was bilateral.

FIG. 6a shows the effect of position along the lens optical axis on the QLS relaxation time of the slow decay mode of intact rabbit lenses of various ages. Note that the lens nucleus (N) exhibits a significantly more intense signal as compared to the anterior cortex.surpanucleus (C) and that this differential signal between those two regions increases as a function of age. The same effects are demonstrated in intact human lenses. FIG. 6b illustrates the ratio of light scattered by the slow and fast scatters. The ratio is very low in the cortex and high in the nucleus. An increase in this ratio in the anterior cortex indicates AD.

DETAILED DESCRIPTION

Figure 1A:
FIGS. 1a-k are a series of photographs showing supranuclear cataracts and cytoplasmic Aβ in the supranuclear/deep cortical region of postmortem lenses from Alzheimer's disease patients.
Figure 1B:
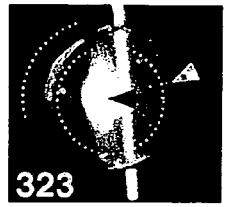
Figure 1C:
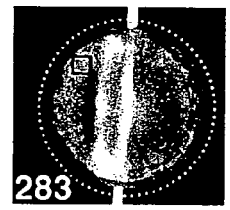
Figure 1D:
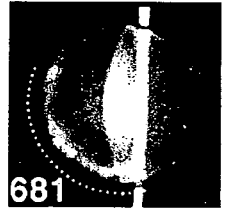
Figure 1E:
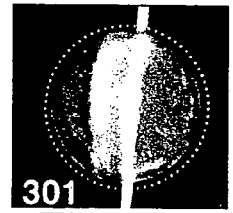
Figure 1F:
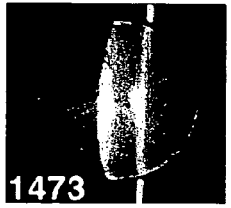
Figure 1G:
Figure 1H:
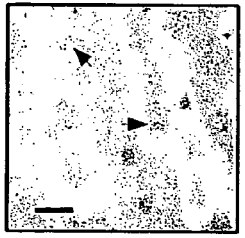
Figure 1I:
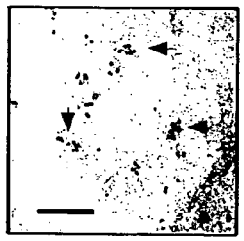
Figure 1J:
Figure 1K:
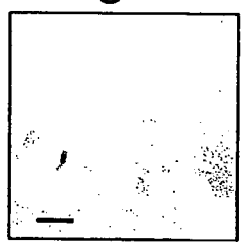

This invention provides for a sensitive means to non-invasively, safely, and reliably detect a biomarker of Alzheimer's Disease (AD) in the lens and other ocular tissues using a quasi-elastic light scattering, Raman spectroscopy, fluorometric or other optical technologies. These techniques allow detection and monitoring of amyloid protein deposition in the eye for the diagnosis of neurodegenerative disorders such as AD and prionopathies. Lens protein aggregation is potentiated by human $A\beta_{1-42}$ peptide, a pathogenic and neurotoxic peptide species which aggregates and accumulates in AD brain. Aβ was found to promote protein aggregation in vivo and in vitro. $A\beta_{1-42}$ was found specifically in the deep cortex and supranucleus of human lenses and was associated with large molecular weight protein aggregates. The results indicate that the protein aggregation in the lens, e.g., in lens cortical fiber cells, represents an easily accessible peripheral marker of AD pathology in the brain.

Lens Architecture and Protein Aggregation

Beneath an acellular capsule on the anterior side of the lens is a cuboidal monolayer of lens epithelial cells (LEC). The central (axial) LECs do not divide but survive throughout life. The more peripheral LECs divide and migrate peripherally toward the lens equator and there begin a process of terminal differentiation (TD) into cortical fiber cells. During TD the intracellular organelles are lost so that in the nucleus, the cells are devoid of most intracellular organelles. Superficial fiber cells at the equatorial region possess nuclei and organelles in varying stages of disintegration, but deeper cortical fiber cells (and all nuclear fiber cells) are devoid of intracellular organelles. In spite of a general sluggish, largely anaerobic metabolism lens fiber cells maintain protein synthesis throughout life, but they lack means to efficiently or completely clear away post-translationally modified proteins. Consequently lens proteins are the most long-lived proteins in the body and they reflect in their post-translational changes the stresses that have affected the lens throughout life. Protein aggregation is one of the post-translational changes, and Aβ-associated aggregation in the lens parallels the aggregation that occurs in AD brain.

The unique features of lens fiber cells foster cellular retention and accumulation of protein. Aβ accumulation and associated protein aggregation within the deep cortical/supranuclear regions of the lens parallels or precedes similar Aβ-mediated amyloidogenic processes in AD-affected brain, thus providing not only non-invasive but also early (pre-symptomatic) detection of the AD disease process. Thus, non-invasive in vivo quantitative assessment of protein aggregation and opacification within the deep cortical/supranuclear region of the human lens is useful for diagnostic detection and tracking of cerebral Aβ accumulation in prodromal or established AD.

Lens protein aggregation associated with age-related cataracts (ARC) differ in composition and location from aggregates or cataracts associated with AD. Postmortem human lenses from seven successive donors with severe AD-related neuropathological changes were examined. All of these donors exhibited supranuclear (deep cortical) cataracts. In five of the seven donors, the supranuclear cataracts were evident bilaterally. Supranuclear cataracts are a relatively rare cataract phenotype (0.3% in a series of 1,976 surgically extracted intracapsular cataracts and are anatomically distinct from age-related nuclear cataracts. Based on the presence of supranuclear cataracts in all seven of these cases, the lower limit of the 95% confidence interval for the populational proportion of patients with severe AD-related neuropathological changes who would also exhibit supranuclear cataracts is at least 56% (based on calculation of binomial distribution confidence intervals). Thus, there was a statistically significant correlation of supranuclear/cortical polypeptide aggregation with neurodegenerative disease. This same bilateral cataract phenotype was also observed in amyloid-bearing APP2576 transgenic mice, an art-recognized model for human AD.

In each of these lenses, supranuclear cataracts were either the only form of cataract present or the most prominent form of cataract. Although a simple supranuclear cataract may be age-related, the prevalence of simple (or pure) supranuclear cataract simply as a consequence of aging is very low (0.3% in a series of 1976 extracted age-related cataracts). "Simple"

means the only region of opacification present in the lens. Supranuclear cataract as a component of mixed ("mixed" meaning more than one region of the lens opaque) age-related cataracts is higher (approximately 30%). Therefore, in the series of seven pairs of AD lenses the, finding of essentially pure supranuclear cataract in all of them constituted an anomously high, and statistically surprising, rate of supranuclear opacification. The association of supranuclear change with neuropathologically-confirmed AD indicated that the supranuclear opacification or aggregate accumulation is a unique lenticular phenotype or signature of AD evident in the lens. Both human data and animal model data indicate that supranuclear protein accumulation and/or opacification is a manifestation of AD-like degenerative change in the lens.

On a microscopic level, supranuclear opacification is a manifestation of light scattering from areas in which the index of refraction varies greatly over short distances (such as from damaged cellular membranes and low-protein "lakes" that appear in between high-protein fiber cytoplasm). At the interface of the low and high protein areas, light is scattered because the indices of refraction of these two areas are so different. That Aβ is a pro-oxidant and capable of damaging cellular membranes suggests that increased Aβ acts like other oxidants (e.g. $H_2O_2$).

Amyloid Biochemistry in Cataract Formation

As described above, aggregates containing Aβ, the pathogenic protein which accumulates in AD, form supranuclear/deep cortical cataracts within the lenses as well as in the brains of Alzheimer's disease patients. Aβ deposits in the lens were found to collect as intracellular aggregates within the cytosol of lens cortical fiber cells. Lens Aβ was quantified and the results showed that it existed as soluble apparent monomeric and dimeric species within the adult human lens at levels comparable to those in normal adult brain. A substantial proportion of lens Aβ is bound to other lens proteins, including the abundant lens structural protein αB-crystallin. Aβ and αB-crystallin exhibited nanomolar intermolecular binding affinity in vitro and co-immunoprecipitated from formic acid-treated human lens homogenates, indicating strong protein-protein association. Human $Aβ_{1-42}$ promotes lens protein aggregation with increased β-sheet content. Aβ-potentiated lens protein aggregation was blocked by metal chelation or reactive oxygen species scavengers, thus demonstrating that metalloprotein redox reactions are involved in this lens protein aggregation process and supranuclear cataract formation in AD.

These results indicate that a pathologic interaction between Aβ and lens proteins occurs. Furthermore, these Aβ-mediated reactions in the lens indicated that amyloidogenic Aβ species, particularly the human $Aβ_{1-42}$ species which is prominently involved in AD pathophysiology, were potent pro-oxidant peptides which fostered lens protein aggregation. and supranuclear/cortical cataract formation.

Methods for Detecting Ocular Protein Aggregates

A method for detecting Aβ-potentiated protein aggregates using DLS technology was developed and tested in transgenic mice (Tg2576), an art-recognized animal model for Alzheimer's disease. A relationship between $hAβ_{1-42}$ and lenticular protein aggregation was shown to provide a facile means for ocular detection of the early onset stage of AD using DLS (or QLS), in Tg2576 mouse. The data indicated that DLS (or QLS) and/or Raman scattering is useful to detect AD in humans.

The major proteins that can scatter light in a human eye lens are α-, β-, and γ-crystallins. Since the crystallins are abundant and large molecules (molecular weight $\sim 10^6$ Daltons), they induce the greatest amount of scattering of light, including laser radiation in dynamic light scattering (DLS) measurements. When the lens protein molecules are aggregated, they give rise to lens opacities. The lens gradually becomes cloudy as a result of light scattering and absorbance, thus hindering light transmission and the ability to focus a sharp image on the retina at the back of the eye.

Methods for measuring DLS, are known in the art, e.g., Benedek, G. B., 1997, Invest. Ophthalmol. Vis. Sci. 38:1911-1921; Betelhiem, et al., 1999, J. Biochem. Biophys. Res. Comm. 261(2):292-297; and U.S. Pat. No. 5,540,226. For example, a monochromatic, coherent, low-powered laser is shined into the lens of a subject such as a human patient. Agglomerated particle dispersions within the lens reflect and scatter the light. Light scattering is detected using a variety of known methods such as a photo multiplier tube, a solid-state photo diode or a charge coupling device. Because of random, Brownian motion of the lenticular protein crystallins, the concentration of the crystallins appears to fluctuate and hence, the intensity of the detected light also fluctuates. However, a temporal autocorrelation function of the photo current is mathematically analyzed to reveal the particle diffusivity. The data reveals the composition and extent of cataractogenesis. An increase in light scattering in the supranuclear and/or cortical region of the lens (alone and/or normalized to the scattering in the lens nucleus, where general aging effects on the lens predominate and/or normalized for age) compared to a known normal value or a normal control subject indicates the presence of protein aggregation associated with a neurodegenerative disease such as AD. This finding, in turn, serves as a biomarker for the AD disease process and hence is of clinical utility in the diagnosis, prognosis, staging, and monitoring of AD or other amyloidogenic disorders.

Although Aβ has been demonstrated in rodent and monkey lens, these earlier studies did not describe its presence in humans, the relationship of deposition relative to a human disease state or severity of the disease. Nor did earlier studies define the presence, localization, or form of a detectable disease-associated phenotype, i.e., aggregates in the supranuclear/cortical lens region (as distinguished from the lens nucleus), a non-invasive diagnostic method for detection of Aβ aggregates, or methods of distinguishing the AD disease process from ongoing degenerative changes in the lens due to age.

The following examples illustrate methods of detecting ocular protein aggregates and use of such methods to diagnose, monitor and stage neurodegenerative disorders.

Example 1

Alzheimer's Disease β-Amyloid Promotes Lens Protein Aggregation and Supranuclear Cataract Formation Alzheimer's disease is characterized by cerebral accumulation of extracellular protein aggregates composed predominantly of β-amyloid Aβ peptides. The data described herein indicate that aggregates containing Aβ also form deep cortical/supranuclear cataracts within the lenses of Alzheimer's disease patients. This cataract phenotype is distinct from common age-related cataracts in the lens nucleus.

Supranuclear/Cortical Versus Age-Related Nuclear Cataracts

The cornea and the crystalline lens of the eye form an optical system that focuses an image on the retina. The lens is comprised of a capsule that covers the entire lens, an anterior epithelial monolayer, concentric layers of lens "fiber" cells that form a superficial cortical region, and a deep nuclear region. The region at the interface of cortex and nucleus is called the supranucleus. In most individuals, the lens becomes more yellow with increasing age, but in only a small percentage of individuals does lens opacification or cataract develop. Increased yellowing has few significant effects on vision, but opacification may lead to blindness. Lens opacification is a manifestation of light scattering by abnormally large protein aggregates. When the diameter of lens protein aggregates is larger than half the wavelength of incident light, light scattering occurs. High molecular weight aggregation occurs throughout the nucleus and the opacity resulting from this is also diffusely evident in this region of the lens. Lens opacification can also occur as a result of abrupt changes in the index of refraction in contiguous areas due to membrane disruption.

When lens opacification is associated with clinically significant visual symptoms (glare, blur, decreased contrast sensitivity) lens opacities are considered cataracts. The incidence and prevalence of lens opacities increase with age, and with people generally living longer, so does the incidence and prevalence of cataract and cataract surgery. There are three major types of common lens opacification: cortical, nuclear, and posterior subcapsular. These may be simple or pure (involving only one lens anatomic zone) or mixed (involving more than one zone). The most common type of cataract is the age-related nuclear cataract. A fourth type of cataract, the supranuclear cataract, involves the zone between the cortex and nucleus (supranucleus), but this cataract in its pure form is relatively rare (<0.5% of cataracts coming to surgery). This low incidence is important since the AD-associated lens pathology described herein is this relatively rare supranuclear cataract, which is easily distinguishable from the much more common age-related nuclear cataract associated with advancing age.

The molecular changes that underlie cortical and posterior subcapsular lens opacification effect primarily lens membranes and are manifested as changes in membrane permeability, loss of structural integrity, and formation of lacunae between cells. These lacunae exhibit a low index of refraction as compared to the relatively high index of refraction of the adjacent cellular cytoplasm, thus creating a light scattering interface. Cortical opacities are spoke-like and usually extend from the equator into the visual axis. Posterior subcapsular cataracts are usually discoid opacities on the posterior capsule in the visual axis. The molecular changes that underlie nuclear opacification are quite different from those involved in cortical cataract and consist of high molecular weight (HMW) aggregate formation. In humans supranuclear cataracts share many of the features of cortical cataracts, but in the early stages there are diffuse fleck-like opacities throughout the supranucleus.

Since the molecular changes underlying cataract begin in early adulthood, it is possible to detect some of these changes with instruments sensitive to light scattering. QLS and Raman spectroscopy are two such techniques. They are used non-invasively to examine the lens through a widely dilated pupil, and each can be focused on a particular region of the lens (cortex, supranucleus, nucleus, posterior subcapsular).

Methods for Differentiating Age-Related Nuclear from AD-Related Lens Changes: Diagnostic Instrumentation QLS yields a measure of the average hydrodynamic radius (molecular size) in a specified region of light scattering. In addition, the relative amounts of high molecular weight and low molecular weight scatterers and the average molecular weight of each of these species within each region can be quantitated from the QLS autocorrelation function. Safe and non-invasive in vivo QLS measurements are quickly determined in human and animal subjects after simple dilation of the pupil. Measurements are readily achieved in lenses ex vivo. These QLS measurements are precisely determined within the different subregional anatomic zones within the lens (i.e., cortex, supranucleus, and nucleus).

QLS measurements in aging lenses has revealed a steady increase with age in the intensity of light coming from high molecular weight scatterers in the lens nucleus. There is a much smaller increase in this type of scattering in the cortex and supranucleus of the normal aging clear lens. In fact, profiles of the light scattering properties of the aging normal human lens reveal a distinct difference between the QLS signals in these two zones. Even with an age-related nuclear cataract, there is little high molecular weight aggregation in the cortical and supranuclear regions. QLS measurements are made using well-characterized cohorts (e.g., normal and AD). Means and standard deviations are determined to characterize group QLS signals for the cortex (C), nucleus (N), and the relative C/N ratio. This latter parameter is a simple ratiometric function which captures and normalizes differences in the cortex (and supranucleus) versus the nucleus which are not accounted for simply by advanced age. Conventional statistical methods are selected a priori and applied to the data sets to determine differences between groups and assess outlier measurements.

Simple QLS ratiometric function (C/N) differentially characterizes normal aging versus AD lenses because the presence of A$\beta$ in the lenses of AD patients accelerates high molecular weight aggregation within the supranucleus and cortical lens regions, but not in the lens nucleus. This is supported by the observation that A$\beta$ accumulates in lens fiber cell cytoplasm in the deep cortex of human lenses, precisely the relatively rare (supranuclear) cataract formation was found in postmortem lens specimens from advanced AD patients. Furthermore, A$\beta$ species, particularly human A$\beta_{1-42}$, potently fosters lens protein aggregation in vitro through mechanisms involving trace metals and generation of reactive oxygen species, including the freely permeable pro-oxidant hydrogen peroxide. The A$\beta$ in the lens cortex and supranucleus fosters lens protein aggregation and membrane damage which is non-invasively and safely measured in human patients. The same method was successfully used in a study of Tg2576 mutant APP transgenic mice.

All known mutations associated with familial Alzheimer's disease ultimately result in increased production and accumulation of cerebral and vascular A$\beta_{1-42}$. This fact supports the widely held view that accumulation and aggregation of A$\beta$ are key pathogenic factors in all forms of the disease. A$\beta$ was found to localize in the cytosolic compartment of lens cortical fiber cells of aged AD patients and dose-dependently promotes lens protein aggregation in vitro. In addition, an unusual deep cortical (supranuclear) cataract was found to be associated with AD. A$\beta$-mediated aggregation events are occur in parallel in these different tissue domains. In the brain, these are pathologically seen as neuritic or diffuse plaques, whereas in the lens this process leads to cortical lens protein aggregation and ultimately supranuclear cataract. The ocular lens reflect these A$\beta$-mediated events at an earlier stage in the AD disease process since the lens has a relatively limited ability to clear damaged or aggregated protein.

The QLS C/N ratio favors higher relative ratios in AD patients compared to age-matched normal controls, indicative of increased A$\beta$-mediated cortical and supranuclear lens protein aggregation and associated membrane damage in AD patients. This ratio is unique in AD, and the increase in the QLS C/N ratio is apparent even in the very early stages of the disease process. In contrast, the QLS C/N ratio in the non-AD aging lens favors lower relative C/N ratios reflecting the comparatively larger contribution of nuclear aggregation of large scatterers and little if any cortical or supranuclear aggregation. Corollaries of this rationale apply to the parameters measured by Raman spectroscopy and grossly observed by slit-lamp examination. These are the fundamental premises on which this diagnostic device for AD is based.

A$\beta$ deposits in the lens collect as intracellular aggregates within the cytosol of lens cortical fiber cells. A$\beta$ also exists as soluble apparent monomeric and dimeric species within the adult human lens at levels comparable to those in normal adult brain. A substantial proportion of A$\beta$ is bound to other lens proteins, including the abundant lens structural protein $\alpha$B-crystallin. A$\beta$ and $\alpha$B-crystallin exhibited nanomolar intermolecular binding affinity in vitro and co-immunoprecipitated from formic acid-treated human lens homogenates, indicating strong protein-protein association. In vitro, human A$\beta_{1-42}$ promoted lens protein aggregation with increased $\beta$-sheet content, a reaction blocked by metal chelation or reactive oxygen species scavengers. These data provide evidence for metalloprotein redox reactions in A$\beta$-mediated protein aggregation and supranuclear cataract formation in Alzheimer's disease. Non-invasive quantitative measurement of protein aggregation and cataract formation within the lens supranuclear region may provide a means for early detection and monitoring of abnormal A$\beta$ metabolism in Alzheimer's disease.

The following materials and methods were used to generate the data described herein.

A$\beta$ Peptides

Human and rat A$\beta$ peptides were synthesized using standard methods.

Human Lenses and Brain

For correlation of lens and cerebral pathology, human lenses were obtained at autopsy from 8 consecutive Alzheimer's disease donor cases (sex: 7 females, 1 male; average age 76.1±7.9 years range: 63-83 years; average post-mortem interval: 8 hrs; range 3-36 hrs. The brain from each donor was removed, fixed in 10% formalin, and examined according to established procedures for diagnosing AD.

Slit Beam Lens Photomicroscopy and Grading

Freshly dissected, unfixed whole lenses were placed in a black Corian® dish containing isotonic TC-199 culture medium at 37° C. Slit beam illuminated stereo photomicrophic images were obtained and graded for cataracts using known methods.

Lens Anti-A$\beta$ Immunoelectron Microscopy

After slit beam photomicroscopic documentation, one lens from each donor was fixed in a solution of 4% paraformaldehyde/0.5% glutaraldehyde in phosphate-buffered saline (PBS), pH 7.4, for 2 hrs at room temperature followed by a 3 day fixation at 4° C. in a solution of 4% paraformaldehyde in PBS. Lenses were post-fixed in a solution of 0.5% paraformaldehyde at 4° C. and then cryoprotected in 2.3 M sucrose. The lenses were then frozen in liquid nitrogen, cryosectioned, and prepared for immunostaining. 4G8 anti-A$\beta$ mAb directed against A$\beta$17-24 (Signet Laboratories, Dedham, Mass.) was used for anti-A$\beta$ immunostaining.

Lens APP and A$\beta$ Western Blots

Human lens and retina were homogenized in 1 ml ice cold PBS containing protease inhibitors, and centrifuged at 350,000×g for 30 min at 4° C. Supernatants were retained as the soluble subcellular fraction. Pellets were extracted in 1 ml homogenization buffer containing 0.5% Triton X-100. Detergent-insoluble material was pelleted by centrifugation and the supernatant (membrane extract) removed.

Precipitation of APP

NaCl concentration and pH of membrane extracts and soluble subcellular fractions were adjusted to 350 mM, pH 8. Macro-Q anion exchange resin (Pharmacia) pre-equilibrated in incubation buffer was added to each sample (50 µl beads per ml). Following washing with fresh incubation buffer, beads were pelleted, and absorbed APP was released by incubation with elution buffer (1 M NaCl in 50 mM Tris, pH 8). Eluates were then electrophoresed on SDS-PAGE, blotted and probed with monoclonal antibody 6E10. Lyophilised lenses were homogenised by sonication in 1 ml of HPLC water and centrifuged at 100,000×g for 1 hour at 4° C. Aliquots of the soluble and insoluble fractions were electrophoresed on Tris-tricine PAGE and Western blotted. $\alpha$B-crystallin and A$\beta$ were detected by rabbit polyclonal anti-human $\alpha$B-crystallin antibody and mouse monoclonal anti-A$\beta$ antibody WO2, respectively. Monomeric A$\beta$ was measured by quantitative enhanced chemiluminescence using standard methods.

Human Total Soluble Lens Protein (hTSLP) Preparation

Human lenses with intact capsules were dissected from whole globes and homogenized in 1 mL HPLC water. The homogenate was centrifuged for at 100,000×g for 1 hour at 4° C. and the supernatant utilized as hTLSP. Protein concentration was determined using a commercially available kit (Pierce). The final hTSLP concentration was 1 mg/mL.

Turbidity Assay

Test solutions of hTSLP (1 mg/ml) were plated to a final volume of 200 µL per well in 96 well microtiter plates with black sidewalls. Peptides and/or inhibitors were added to these solutions as indicated. Plates were incubated in the dark at 37° C. under humidified, $CO_2$-balanced conditions. Turbidity (optical density) was assessed on a SpectraMax-Plus spectrophotometric plate reader set at a wavelength of 400 nm.

Precipitation Study

Solutions of hTSLP (1 mg/ml) were incubated with or without hA$\beta_{1-42}$ (10 µM; 45 µg/ml) for 0 or 7 days. The resulting mixtures were then centrifuged at 15,000×g for 15 min and separated into pellet and supernatant fractions. The amount of pelleted protein was calculated by subtracting the supernatant protein concentration on Day 7 from the initial concentration on Day 0.

Co-Immunoprecipitation

The pelletable fraction of homogenates from three human lens were treated for 2 hours with 1 mL of 70% formic acid, vacuum dried, neutralized, and dissolved in immunoprecipitation buffer containing NaCl (150 mM), EDTA (2 mM), NP-40 (0.25%), Triton X100 (1%) in Tris-HCl (10 mM), pH 7.4.

Immunoprecipitation

2 µL of a rabbit polyclonal anti-human $\alpha$B-crystallin antibody or control rabbit IgG was added to the immunoprecipitation solution, then precipitated and pelleted with goat-anti-rabbit magnetic beads (Pierce). The immunoprecipitated material was extensively washed, dissolved in Nu-Page LDS sample buffer containing 5% $\beta$-mercaptoethanol, and heated to 70° C. for 10 minutes. Positive controls included purified recombinant human $\alpha$B-crystallin and hA$\beta_{1-42}$. Samples were electrophoresed on 4-12% Bis-Tris gels (Invitrogen), Western blotted, and probed with the mouse anti-A$\beta$ mAb 4G8 (Signet) or WO2. Horseradish peroxidase-conjugated anti-mouse antibody with minimal human antigen crossreactivity (Jackson Laboratory) was used for detection. Blots were developed by enhanced chemiluminescence.

Thioflavin-T Fluorescence

Fluorescence assays were conducted according to a standard protocols.

Dynamic Light Scattering

Light scattering assays were carried out using standard protocols and instrumentation, e.g., the method described in Ansari et al., 1999, Diabetes Technol Ther. Summer; 1(2): 159-68.

Detection of Aβ Deposition and Supranuclear Cataracts in AD Lenses

Figure 2A:
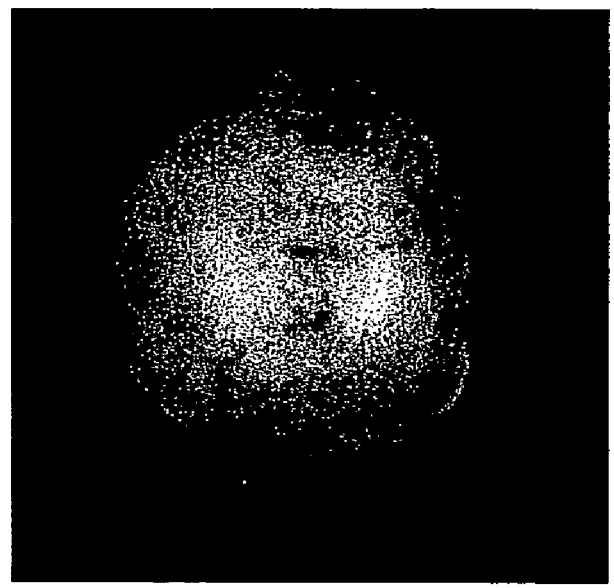
FIG. 2a-b are close-up photographs of a cataract in a 10 month old Tg2576 APPswed transgenic mouse.
Figure 2B:

Postmortem human lenses from seven successive donors with severe AD-related neuropathological changes were examined. All of these donors exhibited supranuclear (deep cortical) cataracts. In five of the seven donors, the supranuclear cataracts were evident bilaterally. Supranuclear cataracts are a relatively rare cataract phenotype (0.3% in a series of 1,976 surgically extracted intracapsular cataracts and are anatomically distinct from age-related nuclear cataracts. The presence of supranuclear cataracts was observed in all seven of these cases, and the same bilateral cataract phenotype was detected in amyloid-bearing APP2576 transgenic mice, an art-recognized mouse model of AD (FIGS. 1a-k). FIG. 2a-b are close-up photographs of a cataract in a 10 month old Tg2576 APPswed transgenic mouse. At 10 months of age, cerebral Aβ is beginning to accumulate in these mice.

Experiments were carried out to determine whether the human supranuclear cataracts were ultrastructurally associated with Aβ deposition. Ultra-thin cyrosections of human AD lens specimens were probed with anti-Aβ monoclonal antibodies (mAbs) directed against intramembranous (mAb 4G8) and extracellular (mAb 6E10) APP domains and examined by immunogold electron microscopy (IEM). Clusters of intracellular Aβ-immunoreactive particles associated with electron-dense microaggregates were found throughout the lens cortical fiber cell cytoplasm in the same lens region in which the supranuclear cataracts were observed. The diameter of these Aβ-associated microaggregates (>100 nm) indicated that these Aβ-associated microaggregates could induce light scattering and lens opacification. Neither extracellular Aβ nor membrane-associated deposits were observed. Minimal immunoreactive material was evident in the epithelial or capsular regions of the lens. Investigation of the lens nucleus was prevented by sclerosis, a common feature of the aged lens. Control sections probed with non-immune antibody or absence of primary antibody did not reveal immunoreactivity. Aβ-immunoreactive staining was not observed in a lens from a normal 14-year old male (control subject). Non-AD adult human lens demonstrated Aβ immunoreactivity, but the intensity was markedly reduced compared to the AD lens. This finding was compatible with the observation that approximately 60% of non-demented individuals over the age of 60 exhibit cerebral amyloid deposition. 4G8 immunoreactivity was not seen in proximity to membrane structures, indicating that the immunoreactivity detected was likely Aβ and not full-length or soluble APP.

The expression of 110 kDa and 130 kDa APP in human lens and retina was confirmed by Western blot analysis using the anti-N-terminal anti-APP mAb, 22C11. Characterization of lens Aβ was performed using an Aβ-specific quantitative Western blot assay with an Aβ detection limit of approximately 0.1 ng. Aβ-immunoreactive bands which migrated at molecular weights equivalent to monomeric (≈4 kDa) and dimeric (≈9 kDa) Aβ were detected in the soluble lens protein fraction. The concentration of combined apparent monomeric and dimeric Aβ species in this fraction of human total lens protein from adult humans (4 males, 7 females; mean age 74.8±9.6 years) was 1.31 µg/g protein, comparable to control aged human brain (2.1 µg/g wet weight cortex. The apparent SDS-resistant Aβ dimer was ten times more abundant than the monomer. SDS-resistant Aβ dimer (but not the Aβ monomer) was also detected in the insoluble lens protein fraction. However, the apparent Aβ monomeric and dimeric species represent only a minor proportion of total lenticular Aβ immunoreactivity. The majority of the Aβ immunoreactivity migrated as a broad range of relatively higher molecular weight material.

Concentration differences in low molecular weight Aβ species may be small in comparison to Aβ which has accumulated as relatively higher molecular weight cross-linked or aggregated material. Western blot analysis of human lens homogenates resolved prominent Aβ-immunoreactive bands of ≈18-25 kDa, ≈60 kDa, and ≈105 kDa, in addition to immunoreactive material which did not resolve as discrete bands. These findings indicated either that numerous multimeric Aβ species are present within the lens or that a proportion of lens Aβ may form SDS-stable hetero-oligomeric complexes with other proteins within the lens fiber cell cytoplasm.

The cytosolic structural protein αB-crystallin (m.w. 20,159 Da) is one of the most abundant proteins in the lens where it accumulates within the long-lived lens fiber cells. Due to limited protein turnover and clearance in these cells, αB-crystallin is retained within the lens with a half-life measured in decades and is subject to cumulative post-translational modification, truncation, oxidation, and cross-linkage. Some of the Aβ immunoreactivity observed in the ≈18-25 kDa range represents binding of Aβ (m.w. 4,513 Da) to truncated and full-length αB-crystallin. Studies were carried out to determine whether Aβ binds to αB-crystallin in vitro. An ELISA assay was used to demonstrate saturable, high-affinity binding of recombinant human αB-crystallin to immobilized synthetic human $A\beta_{1-42}$ or Aβ1-40 with apparent binding constants of ≈20 nM for both Aβ species. This binding was inhibited by addition of excess free (non-immobilized) Aβ.

Since Aβ and αB-crystallin co-localize within the lens fiber cell cytoplasm and bind one another in vitro, it was possible that over time these two proteins may become covalently cross-linked in vivo. Cross-linked Aβ/αB-crystallin hetero-oligomers in postmortem human lenses were examined using a co-immunoprecipitation strategy. Lens protein pellet fractions were prepared from three aged human donors. The pellets were solubilized with 70% formic acid, and the resulting material extracted with a chelator and anionic detergents. Proteins were immunoprecipitated with a polyclonal rabbit anti-human αB-crystallin antibody. Two distinct SDS-resistant co-immunoprecipitating bands, one at ≈25 kDa and the other at ≈80 kDa, were detected in the immunoprecipitate by Western blot using the anti-Aβ mAb 4G8. The co-immunoprecipitating band at ≈25 kDa shows an approximate +4 kDa shift (equivalent to monomeric Aβ) with respect to αB-crystallin. The same results were obtained when the blots were stripped and reprobed with the WO2 anti-Aβ mAb. A control blot in which the primary anti-Aβ antibody was excluded did not produce signals. Crossreactivity between the co-immunoprecipitating and Western blot antibodies was not observed. These findings indicated that these two proteins are tightly associated in the insoluble protein fraction of the lens. Stability of these anti-Aβ/αB-crystallin immunoreactive species to formic acid, anionic detergents, metal chelation, denaturation, and reducing conditions is compatible with covalent protein cross-linkage.

Experiments were carried out to determine whether similar Aβ/αB-crystallin complexes could be generated in vitro. hTSLP was incubated for 7 days with synthetic human $A\beta_{1-42}$ ($hA\beta_{1-42}$) and analyzed by co-immunoprecipitation and Western blotting. Immunoreactive bands migrating at ≈25 kDa and ≈80 kDa were detected on Aβ Western blot, providing further support for hetero-oligomeric cross-linking of Aβ and αB-crystallin within the lens.

Aβ-to-αB-crystallin cross-linkage in the lens involves $H_2O_2$-mediated oxidative reactions. The lens is a highly oxidative environment which fosters lens protein cross-linking. Furthermore, Aβ itself generates hydrogen peroxide through metalloprotein redox reactions involving complexation with Cu(II) or Fe(III). These findings are pertinent in light of copper and iron enrichment in AD brain and cataractous lens. Therefore, Aβ-potentiated lens protein aggregation may also be mediated through metalloprotein redox reactions. The data showed that incubation of hTSLP with $hA\beta_{1-42}$ resulted in a dose-dependent of hTSLP aggregation potentiation. Anti-Aβ IEM revealed large (>100 nm) amorphous electron dense immunoreactive material which was observed only in solutions containing both hTSLP and $hA\beta_{1-42}$. Aβ-potentiated hTSLP aggregation is not due exclusively to Aβ autoaggregation, since there was minimal aggregation in $hA\beta_{1-42}$ control solutions. Furthermore, Aβ-potentiated hTSLP aggregation can involve precipitation of additional non-Aβ lens proteins since co-incubation of $hA\beta_{1-42}$ (45 µg/ml) and hTSLP (1 mg/ml) for 7 days resulted in a pelletable precipitate of approximately 21% (>200 ng) of the total incubated protein. This quantity of precipitated protein is at least 4-times greater than the combined total of exogenously added Aβ (45 µg), and endogenous Aβ (≈1 ng), indicating that additional lens proteins other than Aβ are contained within the protein precipitate. Aβ-mediated lens protein aggregation is also peptide-specific. Unlike the highly redox-active $hA\beta_{1-42}$, none of the relatively redox inert control peptides (synthetic human Aβ1-40, synthetic rat Aβ1-40, or recombinant human insulin) promoted hTSLP aggregation.

To determine whether the Aβ-induced aggregation of hTSLP was accompanied by conformational changes, the total β-sheet content of the protein mixture was measured by monitoring thioflavin-T fluorescence. Solutions of hTSLP incubated with $hA\beta_{1-42}$ exhibited markedly increased thioflavin-T fluorescence compared to hTSLP alone, indicating that Aβ-potentiated hTSLP aggregation is associated with enhanced β-sheet content.

DLS was used to investigate the kinetics and change in mean hydrodynamic diameter of Aβ-potentiated hTSLP aggregation. Incubation of $hA\beta_{1-42}$ with hTSLP resulted in sigmoidal aggregation kinetics with a steep inflection point, indicative of a critical nucleation event. The size of the largest scatterers was several hundreds of nanometers (mean, 244 nm; variance, 0.935; skew, 1.469), consistent with the size of the large amorphous electron-dense Aβ-immunoreactive material seen by IEM. Similar kinetics were not observed in solutions of hTSLP without added Aβ. Solutions of αB-crystallin incubated with $hA\beta_{1-42}$ did not exhibit an increase in mean hydrodynamic diameter over time, suggesting that the relatively higher α-crystallin chaperoning capacity in this solution mitigated the $hA\beta_{1-42}$ pro-aggregant effect, or alternatively, that a stochastic event was not captured during the experiment. By contrast, solutions of pure $hA\beta_{1-42}$ in the absence of hTSLP exhibited an immediately evident and persistently fluctuating wide-amplitude signal consistent with intermittent passage of large aggregates through the laser light path.

$H_2O_2$ production by $hA\beta_{1-42}$ is dependent on Cu(II) or Fe(III) binding and subsequent peptide-centered metal reduction. Both of these redox-active metal ions are present in adult human lens homogenate supernatant (µg/gr protein: Fe, 5.97±2.28; Cu, 1.81±1.55) and pellet fractions (µg/gr protein: Fe, 11.98±12.52; Cu, 1.25±0.44). The role of metalloprotein redox chemistry in Aβ-potentiated hTSLP aggregation was tested by adding the metal chelator diethylenetriaminepentaacetic acid (DTPA; absolute log Ks for Fe, 28.1; Cu, 22.0; and Zn, 19.3) or antioxidant scavenging enzymes catalase and superoxide dismutase during incubation. These interventions abolished aggregation, and similarly blocked increased β-sheet content and protein precipitation. These data support a role for metalloprotein redox reactions in Aβ-potentiated lens protein aggregation.

These findings indicate that the supranuclear cataract phenotype in lenses from AD-affected patients is a reflection of the same abnormality of Aβ biochemistry that causes regionally specific cerebral Aβ accumulation in AD. Lens and brain Aβ aggregation differ in that the ultrastructural localization of Aβ deposits in the lens is exclusively within the cortical fiber cell cytoplasm in contrast to the predominantly extracellular deposition observed in AD-affected neocortex. Aβ and αB-crystallin not only co-localize within the intracellular compartment of the lens fiber cells, but also associate and cross-link. Aβ-mediated lens protein aggregation other cytosolic lens proteins including αA-crystallin, β-crystallins, and γ-crystallins.

The data supports an intracellular redox-active metal dependent oxidative cross-linking mechanism for Aβ-lens protein interactions which is similar to the extracellular reaction series proposed for Aβ autoaggregation. $H_2O_2$ produced by Aβ is exaggerated by Cu(II) bound to the peptide and results in simultaneous metal reduction. These reaction products are classical Fenton chemistry substrates which generate the hydroxyl radical. Hydroxylated amino acids have been identified in cataractous lens proteins. Based on the high-affinity binding of αB-crystallin to Aβ, these proteins are expected to associate within lens cortical fiber cell cytoplasm. Hydroxyl radical decay in the vicinity of Aβ or αB-crystallin could radicalize either protein, potentially resulting in covalent protein cross-linkage. Copper levels are elevated in cataractous lens and in AD-affected brain, factors which may contribute to protein cross-linkage and aggregation. α-crystallins are vulnerable to redox active metal-mediated covalent polymerization. Thus, Aβ in the cytoplasmic compartment of the lens fiber cells may also promote cross-linkage of lens proteins such as αB-crystallin by similar mechanisms.

Example 2

Preparation of Lenticular Protein

Human and bovine lenses were dissected under a laminar flow hood using standard methods. A scalpel was used to make incisions at the junction between the cornea and the sclera large enough to insert the tip of a small pair of scissors. Warm phosphate buffered saline (PBS) was then injected between the cornea and the lens. The scissors were used to cut around the cornea which could then be removed and kept for further experiments. After cutting around the iris, the lens was exposed and resting on the vitreous. Four diametrically opposed anteroposterior incisions in the sclera were made so as to put the sclera flat on the table as four quadrants linked near the fovea. The lens was the lifted from the vitreous, and the ligaments that attach the lens loosely to the vitreous as well as the zonular muscles were cut. Careful dissection kept the capsule and epithelial layer intact. Finally, the lens is rolled onto its equator and the remainders of the zonular muscles (black "circle" around the lens) were removed.

Lens homogenates were prepared as follows. A dissected lens and 1 mL of ice cold HPLC water was introduced into a glass Potter homogenizer (volume 1 mL). This mixture was carefully homogenized using slow twisting and vertical motions. Because homogenizing heats up the sample, and grinding of proteins produces free radicals, the homogenization process was performed at 0° C. on ice. The homogenized solution was centrifuged (30,000 rpm) in a polypropylene tube for 1 Hour at 4° C. The resulting supernatant, which contains the soluble fraction of the lens proteins, was collected. Lens protein concentration was assessed by BCA assay (Pierce, Rockford, Ill.) against BSA standards. The centrifuged pellet was kept for further experimentation. For storage purposes, the pellet was washed two times in 1 mL ice cold HPLC water (and centrifuged between washings as described above). The protein concentration of the pellet was assessed by resuspending the pellet via sonication in HPLC water and performing a BCA assay as described above.

Filtered phosphate buffered saline solution (pH 7.4) was treated with chelex and used to make stock solutions (10×) for all reagents (chemical or biological). Protein stock solution at a concentration of 10 mg/mL was prepared from the supernatant as described above. Stock solutions of chelators (ethylenediaminetetraacetic acid (EDTA), diethylenetriaminepentaacetic acid (DTPA), or triethylenetetramine (TETA)) were made up at a concentration of 2 mM freshly prepared in PBS. Stock solutions of Catalase and SOD were freshly prepared in PBS to have an activity of 5000 U/mL and 1000 U/mL respectively. Aβ was prepared as a suspension (100 uM) in PBS or HPLC water by sonicating for three minutes such that only monomers or dimers remained. Metals were prepared as a 10 μM solution; Cu is prepared as Cu:glycine (1:6) from copper sulfate.

Aggregation experiments were carried out in 96 well black micro titer plates, in the 2dark. Depending on the experiment, a combination of 20 μL of 10× lenticular protein (final concentration 1 mg/mL), 20 μL of 10× chelator solution (final concentration 200 μM), 20 μL of Catalase and/or SOD (final concentrations of 500 U/mL and 100 U/mL respectively), 20 μL of Aβ (final concentration of 10 μM), 20 μL of metal solution (final concentration 1 μM), and an amount of PBS buffer to bring the total volume in the well to 200 μL. hTLP aggregation or bTLP aggregation was monitored by observing an increase in absorbance at 400 nm using a Spectramax UV-V is spectrophotometer. The method of the present invention assesses the turbidity (optical density) of the solution and hence the size and number of the aggregates present.

Freshly prepared hTLP and bTLP spontaneously self aggregate at 37° C. in the dark. Aggregation reaches a plateau after 4 days. Hence a 6 day time period is an ideal time point to assess aggregation state. bTLP spontaneous aggregation was analyzed in the presence and absence of metal ion chelators. Cu(II) induces bTLP aggregation; and the presences of some chelators (EDTA, DTPA) reduces the extent of bTLP aggregation. The influence of Reactive Oxygen Species ((ROS), Cu/Zn Superoxide Dismutase (SOD), Catalase (Cat)) on spontaneous bTLP aggregation was analyzed. The data showed that Catalase and/or SOD reduces the extent of bTLP aggregation. The data also indicated that $hA\beta_{1-42}$ ($hA\beta_{42}$) potentiates hTLP aggregation to a much greater extent than either $hA\beta_{1-40}$ ($hA\beta$) or rat $A\beta_{1-40}$ ($rA\beta_{40}$). Moreover, insulin (approximately the same molecular weight of Aβ) serves as a negative control and indicates no effect on hTLP aggregation. hTLP aggregation was determined as a function of $hA\beta_{1-42}$ concentration. In the absence of hTLP, there is no dramatic increase in $A_{400}$ with an increase in $A\beta_{1-42}$. A linear correlation between $hA\beta_{1-42}$ concentration and hTLP aggregation was observed.

Example 3

Use of DLS Instrumentation to Diagnose AD

The light scattered by protein aggregates varies with the size of an aggregate. The hydrodynamic radius (size) of a protein is inferred from its light scattering properties. In the cortical region of the lens, protein aggregation as an age-dependent process is minimal. In the nucleus, however, protein aggregation occurs as a normal age-dependant process. In the diagnostic method described herein, the cortical and supranuclear regions of the lens are evaluated for protein aggregation.

Population-derived data of the light scattering properties of the cortical and supranuclear regions of the lens of normal (and AD) individuals. These data yield means for aggregate size in the cortex and supranculeus. The light scattering data from a patient suspected to have AD or at risk for AD is compared to these means and the significance of the difference used to assign a probability score as to the likelihood that aging alone accounts for the size of the aggregate. In the case of the +AD patient, the likelihood that aging alone accounts for the size of the aggregate will be very low. In the case of the −AD patients the significance of the difference between the patient's mean and the population mean will be low, and age will be the likely basis on which the aggregation occurred.

For fluorescence emission or Raman spectroscopy studies, light emissions are optically filtered to generate an emission signature. The signature is based on a characteristic fluorescence emission with a defined exciting light or a new or modified band on a Raman spectrum. The accumulation of Aβ, Aβ aggregates, and/or Aβ-alpha-crystallin aggregates are the sources of this signature. Such a signature appears in advance of the aggregation, indicating that these signals offer an early means of detecting the abnormal accumulation of Aβ in the lens and therefore evolving AD.

Since the signature of an abnormal protein, e.g., Aβ, or a protein aggregate is defined by comparing two measures from the same lens at different times (or comparing a patient-derived spectral pattern to a population norm), a probability score is assigned to the measured differences in the signature reflecting the likelihood of aging or chance alone being explanations of the differences observed. For example, if the probability score is low, then age (or other random factors) is not likely to explain the differences observed. Since there is likely to be a basal level of age-dependent, AD-independent Aβ accumulation in the lens, the mere detection of a signature of Abeta is not enough to rule in AD. This signature must indicate either more Abeta, or more rapidly accumulating Abeta, than would be expected in the normal aging individual.

The light scattering properties of AD and normal lenses are determined. If the amount of normal, age-dependent Aβ accumulation is to low, then the mere appearance of the signature is clinically significant and predictive of an increased risk of developing AD. Relative amounts of Aβ or Aβ-alpha crystallin aggregates is determined by detecting a unique light fluorescent or Raman signature.

The detection instrument includes two components—a means of visualizing the pupil and slit image of the lens and a means of delivering light to and detecting light scattered from the eye. The visualization device may be a conventional slit lamp or it may be a simple fiber optic video camera and a slit light source. The configuration of the visualization device depends on the method one uses to register (locate) the light scattering device.

If one uses visual criteria to register the light scattering device, then a corneal analyzer and/or a slitlamp with Scheimpflug optics is not be needed. To obtain data from the cortical and/or supranuclear region of the lens, the method is carried out by focusing on the margin of the pupil and taking a measurement at a specified distance (e.g. 0.5-0.9 mm) posterior to this focal plane. The thickness of most adult cortices is 1.0 mm. A measurement at this locus yields data pertinent to the deep cortex and supranucleus.

If one uses an A-scan ultrasound to detect the acoustic surfaces of the eye (anterior cornea, posterior cornea, anterior chamber, anterior lens capsule, cortico-nuclear interfaces, and posterior capsule) then visualizing the point at which the light scattering measures are taken is not necessary. With ultrasonically derived loci, one would specify a measurement locus at a distance of 0.5-0.9 mm posterior to the anterior capsule and take the measurement there. These parameters also yield data from the deep cortex and supranucleus.

Delivery and Detection Optics

A fiber optic for the delivery system is connected to a laser source and the beam leaving the fiberoptic system is delivered through a set of lenses that focuses the light on a small region in the lens. The angle of convergence should be fairly steep so that the angle of divergence is similarly steep. This configuration allows not only a sharp focal region within the cortex, but also insures that the light exiting from the back of the natural lens was similarly divergent and of low energy when it reached the retina. A separate fiberoptic/lens combination is used to detect scattered light. The light collected by this probe is delivered to a photomultimplier tube and the signals from this tube delivered to an autocorrelator linked to a computer. Both the delivery and detection optics may be located in the same metal head. Although this might be an efficient design, it also means that the light detected is light that is almost perfectly back-scattered rather than light scattered more to the side.

In some embodiments, the probe is used with an ophthalmic slit-lamp, corneal analyzer, or a Scheimpflug imaging device. The probe is placed 1 to 10 mm from the lens of the patient, a beam delivered to eye tissue, and emitted light detected. The delivery probe is connected to a laser and a detector. Any QLS or DLS detection system can be used with the method. Such devices and probes are known in the art, e.g., U.S. Pat. No. 5,540,226 or 5,973,779. For example, the fiber-optic probe contains a first connector for mating with a laser module, a second connector for mating with a detector module, a body having a lens housing and a fiber housing, a first optical fiber extending from the first connector to the fiber housing for transmitting laser light, a second optical fiber extending from the second connector to the fiber housing for collecting scattered, reflected, or emitted light, and, a flexible cable surrounding each the optical fiber extending from a position adjacent the connectors to the body. The lens housing is provided with a first quarter pitch, graded index microlens for transmitting light, and a second quarter pitch, graded index microlens for receiving light; and, the fiber housing is provided with ferrules through which each of the optical fibers may extend.

The delivery probe transmits a coherent laser light and focuses the light into a small volume in a patient's eye, e.g., focusing the light in various regions of the lens, aqueous humor, vitreous humor, retina, pupil or iris of the patient's eye. Light that is scattered or emitted by the ocular protein aggregates in the eye is detected using a photo diode, a charge coupling device or a light sensor. Detected light is analyzed with a digital correlator to yield a time autocorrelation function, thereby allowing a determination of a diffusion coefficient of the protein aggregates from the slope of the time autocorrelation function. The globular diameter of an ocular protein aggregate is calculated using the diffusion coefficient and its relationship to ocular temperature, viscosity, and refractive index. The mean diffusion coefficients of the large and small aggregates is measured. In cases in which there are distinct populations of large and small scatterers, a biphasic downsloping curve with a steep decline is obtained (for the small aggregates that oscillate at a fast rate). A curve with a much a lower slope is obtained for the large aggregates that oscillate at a slower rate. The mean diffusion coefficient of these two populations is characterized to derive a ratio of the high MW/low MW scatterers. It is this ratio that is likely to remain low throughout life in the cortex of a normal individual and increase in the cortex of a patient with AD.

These measures of QLS or DLS are easily and reliably interpreted in eyes in which there are no (or few avoidable) overt opacities which increase the level of static (as opposed to dynamic) scatter. Thus, the methods represent a powerful tool for early diagnosis of AD onset or a predisposition to develop AD in relatively younger subjects (e.g., less than 45 years of age) without age-related lens opacity. For example, the methods are used for early detection of AD or evolving AD-related changes in individuals between 30 and 40 years of age. The ability of QLS/DLS to detect Aβ aggregates in the clear lens before any frank opacities develop is a unique and important feature for early detection of AD and related neuropathologies. When there is a high level of static scatter as in an area of frank opacification, the dynamic part of the signals may be "buried" in the static scatter and interpretation is difficult. In the latter case, supranuclear/cortical aggregates are distinguished from nuclear aggregates using standard techniques such as slit lamp illumination. Supranuclear/cortical opacification is graded using standard indices, e.g., LOCS III or Cooperative Cataract Research Group (CCRG) grading system (Chylack et al., 1983, Invest. Optham. and Vis. Sci. 24:424-431). An increase in the amount of opacification in the supranuclear/cortical region of a subject compared to a normal control indicates a diagnosis or predisposition to develop AD. In patients with age-related nuclear cataracts, this determination is made independent of QLS.

The probe is optionally used in conjunction with optical diagnostic techniques of Raman scattering and related Raman methods, e.g., enhanced Raman techniques. In Raman mode, detected scattered light is absorbed via a digital correlator to yield an absorbance spectrum signature which identifies a protein based on the nature of interatomic bonds and vibrational states of the ocular protein aggregates. A Raman spectrum includes peaks, which represent light scattered by specific interatomic bonds. Disulfide and thiol bonds are detectable with Raman, and therefore changes in the number of these bonds/unit of protein is determined. A unique Raman signature is determined for Aβ or an aggregate of Abeta and alpha-crystallin, and detection of the signature in the lens indicates a diagnosis of AD or predisposition to develop AD or related neurodegenerative disease.

The methods are useful to identify the ocular location and composition of an aggregate as well as to measure the concentration or size of aggregates. For example, in QLS/DLS mode, the methods provide data regarding the size of aggregates, and in Raman mode, the methods provide data regarding the specific interatomic bonds in the aggregate. A reduction in the size or concentration of aggregates over time indicates a favorable prognosis or favorable response to therapy. The unique signature of Aβ affords an opportunity to detect Aβ with Raman spectroscopy in the lens, and the size of this unique signal is related to the amount of Aβ in the cortex and supranucleus. Presence of Aβ in the cortex and supranucleus of the lens is a peripherally accessible biomarker of the neurological disease process associated with AD. Changes over time provide a means of monitoring the course of AD and/or the response to treatment of AD.

The methods are specifically directed to measuring the presence of Aβ signals in the supranuclear/cortical lens regions (and optionally in other ocular tissues such as the vitreous humor, aqueous humor, and cornea). The data is expressed as a ratio (ratiometric) or volumetrically. For example, with respect to the lens, data generated in the supranuclear/cortical region (reflecting detection of aggregates associated with the neurological disease process) is expressed as a ratio relative to the same measurements in the nucleus of the lens (where signals are attributable to more global effects of aging). Alternatively, the data is expressed volumetrically. For example, detection of aggregates occupying at least 10% of the volume of the supranuclear/cortical region of the lens indicates a diagnosis of AD or a predisposition thereto. An increase in the % volume (e.g., 20, 30, 40, 50, 75, and up to 100%) indicates a more severe disease state. An increase in the rate of aggregate accumulation also indicates a relatively more severe disease state.

A DLS device contains a small fiber optic probe, e.g., one about the size of a pencil. DLS fiber-optic probes, e.g., a probe described in U.S. Pat. No. 5,973,779, allows accurate, and extremely sensitive particle sizing measurements in fluid dispersions and suspensions such as human ocular tissue without directly contacting the tissue with the device. The probe detects protein crystals or aggregates suspended in the fluid inside the eye or in cells. Light scattering data provides information regarding the size and size distributions of macromolecular particles in the eye. Such particles include proteins in the lens, and collagen fibers and hyaluronic acid molecules in the vitreous humor. The probes, e.g., shown in FIGS. 3a-d, are used in imaging applications, laser Doppler velocimetry, and Raman spectroscopic measurements. Probes are compact, portable, rugged, are free of optical alignment requirements, and offer point and shoot operation for various on-line field applications under various challenging environments. The probes are also extremely flexible in regards to sample container sizes, materials, and shapes. They are suitable for non-invasive analyses of human eye tissues as well as for in vivo experiments in small animals such as transgenic mice. No external vibration isolation and no index matching are required.

An optical fiber transmits a light beam of defined wavelength. For example, the beam is a low-power laser beam. There is little or no risk of eye damage due to the very low power of the laser beam. Light scattered from within the eye back to the instrument is detect by a second optical fiber. The light scatter data may be directed to a computer containing a digital correlator to record the pattern of light for an individual subject. A change in protein particle size, e.g. an increase compared to a normal control, indicates a pathological state.

The DLS probe is capable of measuring the size of particles as small as 1 nm to as large as a few microns in a wide concentration range from very dilute (water-like) dispersions to very turbid (milk-like) suspensions. It is safe and fast to use as it only requires very low laser power (few micro wafts) with very short data acquisition times (2-5 seconds).

Methods using DLS technology have been used to study cataract mechanism at the biochemical and biophysical level (Ansari et al., 1996, J. Crystal Growth 168:216-226). The procedure is adaptable to various state-of-the-art ophthalmic instruments (e.g., slit-lamp, corneal analyzers, and Scheimpflug imaging), thereby allowing ophthalmic diagnosis from visual and photographic observations and at a molecular level. DLS detects and quantifies the early changes associated with diabetes in the vitreous (a fluid in the back of the eye that occupies 80% volume of the eye globe). The pattern of light scattering derived from Aβ aggregates in the supranuclear region of the eye is distinguished from scattering data derived from age-related cataracts and vitreous changes related to diabetes. Most ocular protein aggregates are less than 1000 nm in diameter, e.g., approximately 400 nm. AD-associated aggregates differ from other ocular aggregates by size and location.

The range of aggregate size is determined from i) normed age-adjusted samples of normal and high-probability AD patients during our planned clinical trial, and ii) normalized by simple ratiometric methods (C/N ratio). The larger the aggregates, the more light scattering, and thus, the more opacification, ultimately resulting in a bona fide cataract. Also, the larger the C/N QLS ratio, the greater the probability of AD. For example, detection of aggregates in the supranuclear region of the lens ranging in diameter from greater than 100 nm to greater than 5000 nm is indicative of AD (or a predisposition thereto) when localized to the supranuclear/cortical region.

Figure 3A:
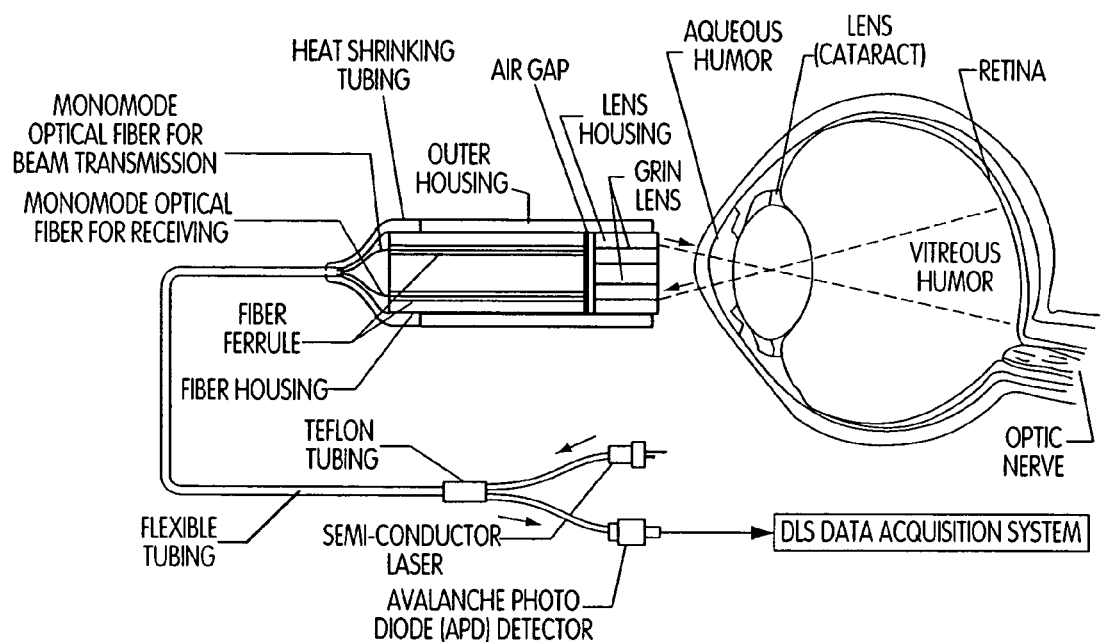
FIG. 3a is a diagram of a Dynamic Light Scattering (DLS) probe emitting light into an eye and returning detected light to a DLS data acquisition system.
Figure 3B:
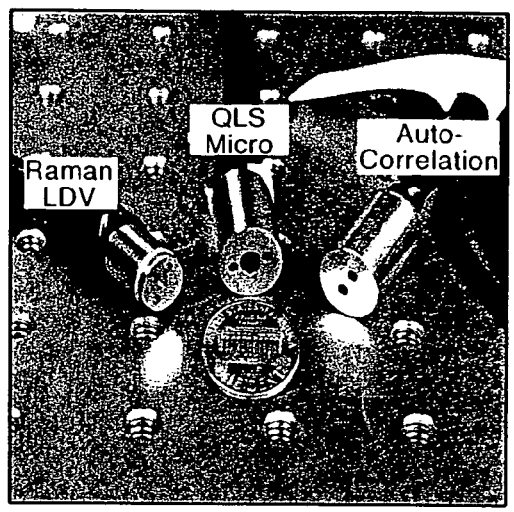
FIG. 3b is a photograph of components of a detection device: a Raman LDV, a QLS micro probe, an autocorrelator. A photograph of a penny is shown to illustrate relative size of the device components.
Figure 3C:
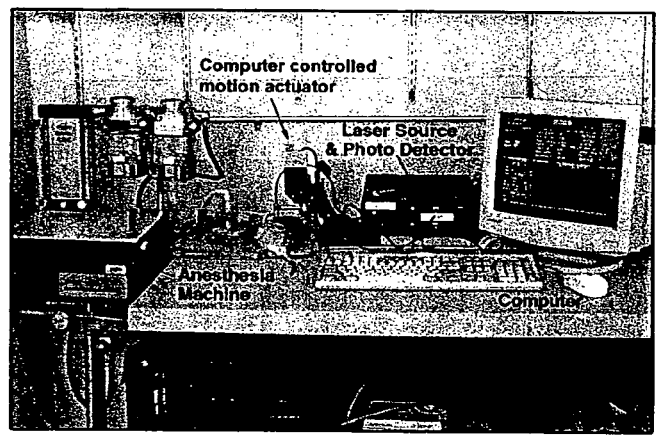
FIGS. 3c and 3d are photographs showing an apparatus and subject (mouse) undergoing in vivo experimental DLS analysis.
Figure 3D:
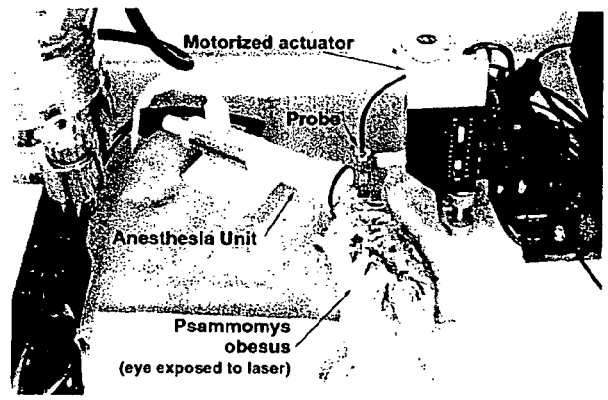
Figure 4:
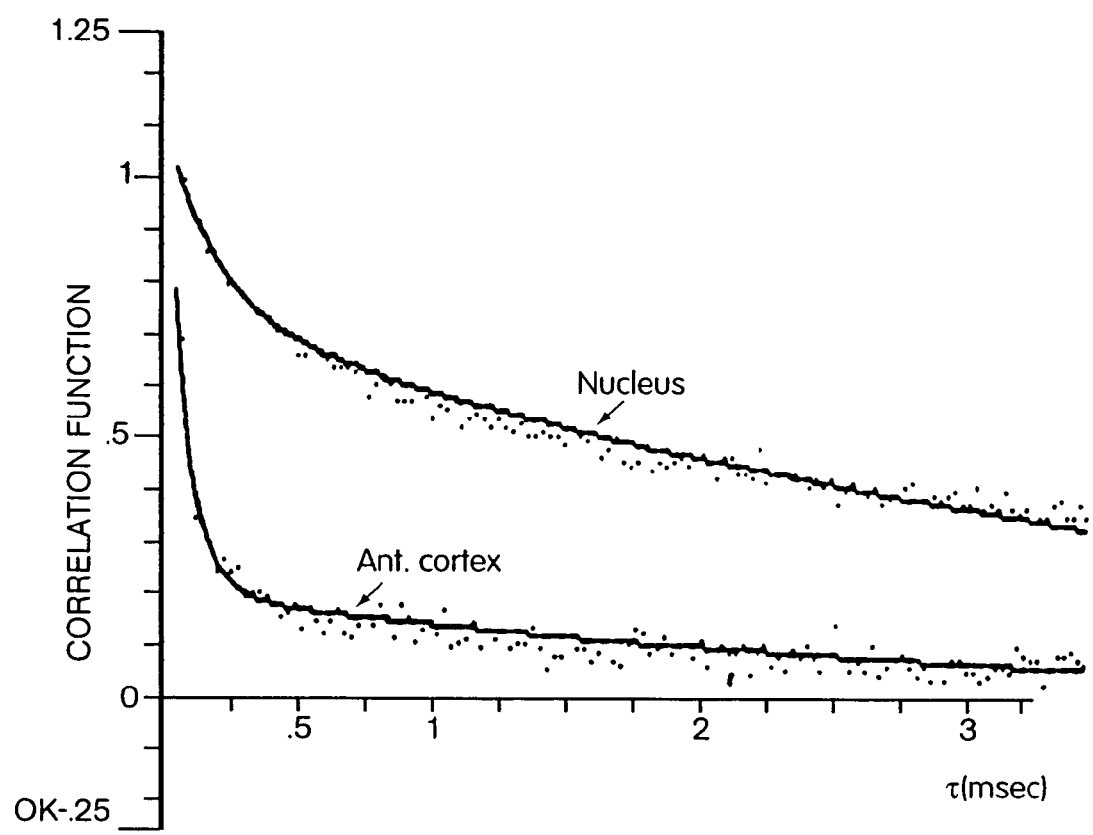
FIG. 4 is a line graph showing in vivo QLS correlation curves from the nucleus and anterior cortex of 6 wk old rabbit. Sample time is μsec. The point represent two experimental correlation curves which have been fitted to the characteristics double exponential decay functions indicated by the lines. These curves illustrated the I(fast) and 1(slow) components of the correlation curve. The intensity of light scattered from the anterior cortex is due to smaller, more rapidly moving scatterers (lower curve), whereas the intensity of scattered light emanating from the nucleus is primarily attributable to larger, more slowly moving scatterers (upper curve).
Figure 5:
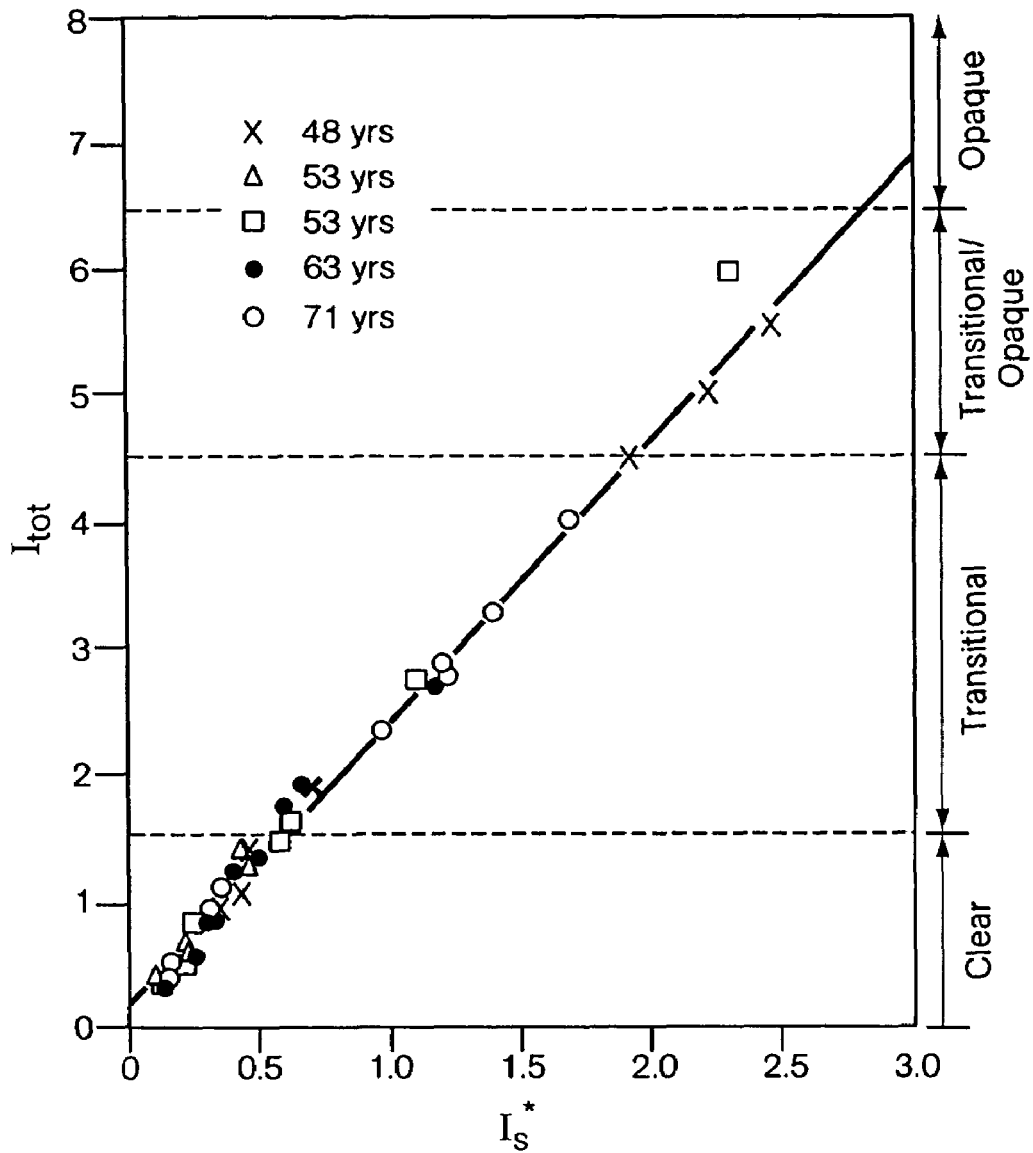
FIG. 5 is a line graph showing a plot of I(tot) vs. I(slow) for five preoperative human cataract patients at various positions along or at near the optical axis of the lens. Independent measurements of I(tot) and I(slow) were made at 5-6 positions ranging from the anterior cortex to the posterior nucleus. This graph illustrates the almost linear relationship between I(tot) and I(slow) for these patients at multiple sites in the lens. These data demonstrate the relationship between the QLS measure of I(total) and I(slow) and the importance of I(slow) as a measure of cataract.
Figure 6A:
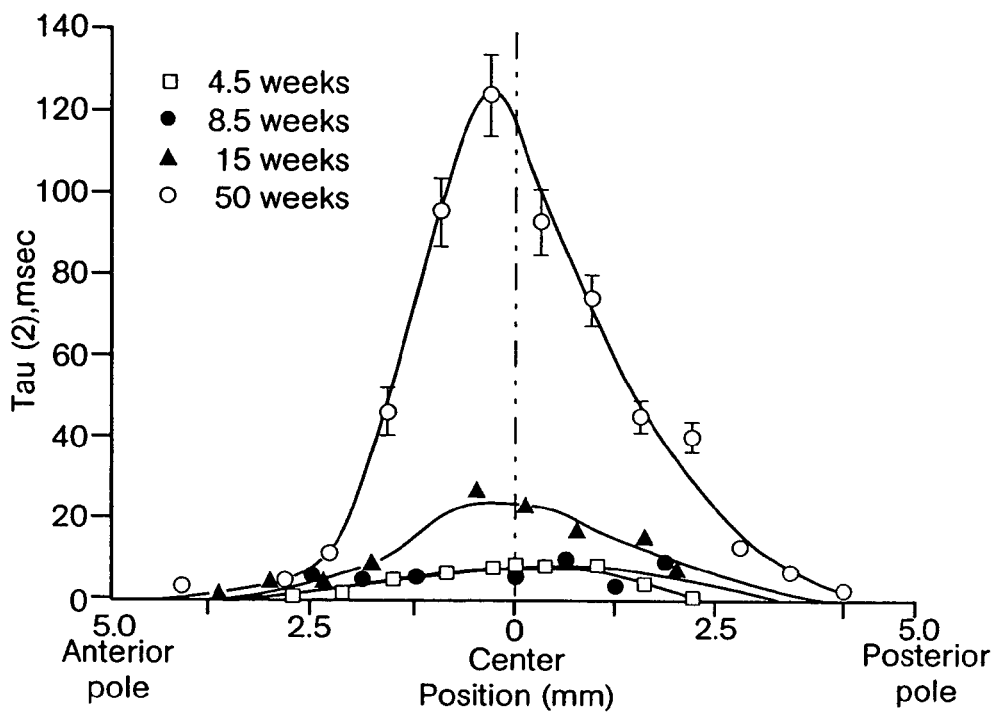
FIGS. 6a-b are line graphs showing data from QLS determinations of ocular tissue.
Figure 6B:
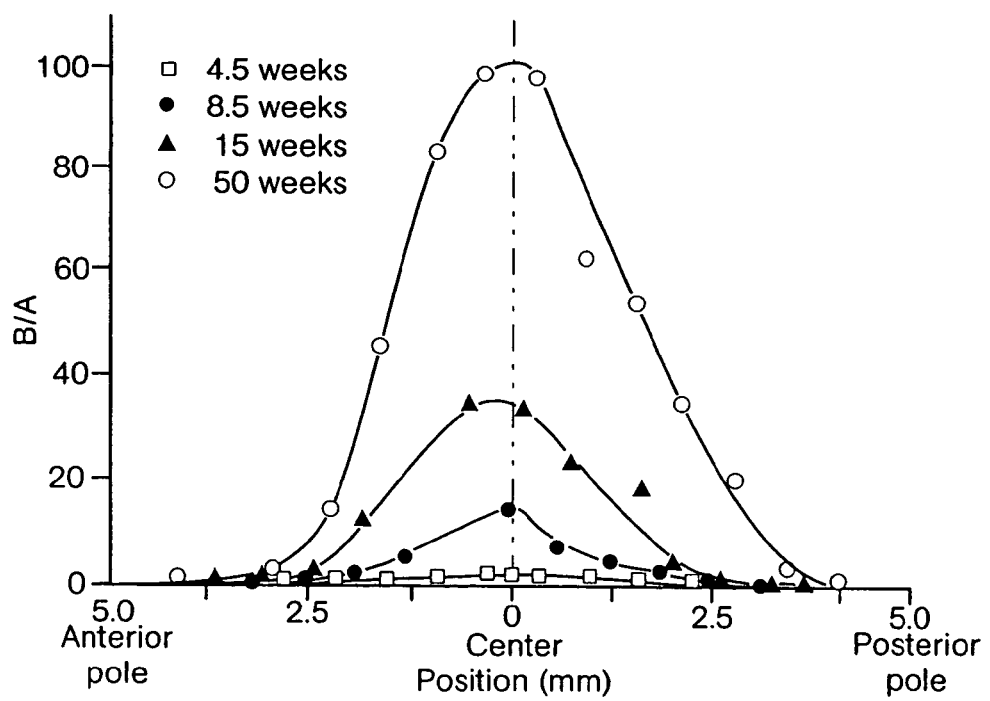

A fiber optic probe containing two monomode optical fibers and two graded index (GRIN) micro lenses provides a compact and remote means of studying the dynamical characteristics of the macromolecules in the eye. The probe is non-invasive and is positioned a few millimeters, e.g., 1-10 mm, in front of the cornea of the eye. The probe has no physical contact with any part of the eye. The laser light out of a laser/detector module is transmitted by a compact backscatter fiber optic probe to the eye. FIG. 3a diagrammatically shows how a target region of an eye is analyzed to detect the presence of aggregates and/or cataracts. FIG. 3b shows a closeup photograph of device components, and FIGS. 3c-d show a mouse undergoing the diagnostic procedure.

Due to the fact that the cornea does not transmit light of wavelengths >392 nm, the wavelengths to be used are in the very near-UV (392-400 nm) or visible (400-?700 nm) range. Light scattering experiments in the eye often use red rather than blue light, since a variable amount of blue light can be absorbed by the pigments in the lens. The more yellow or brown the lens, the more blue light will be absorbed. Some wavelengths longer than blue will excite fluorescence and those should be avoided. With these exceptions, any wavelength may be used in the diagnostic methods described herein.

For the fluorescence experiments, any one of the three 5-10 nm bands in the visible range that excite fluorescence in the lens is used. The accumulation of the Aβ is associated with a change in the wavelength of the emitted fluorescence using the standard exciting wavelengths. Using scanning fluorescent spectroscopy, it is possible to measure in vitro the emitted fluorescence to all wavelengths between 392-700 nm to identify fluorphors associated with Abeta accumulation. The fluorescence emission spectrum of purified Aβ is determined over the same range of exciting wavelengths. An emission spectrum is determined using Aβ in the presence and absence of crystallin proteins to ascertain if a unique fluorescent signature appears when Abeta accumulates or when Abeta binds to a crystallin protein such as alpha-crystallin. Ratiometric measures are derived using one or more, e.g, two, exciting wavelengths.

Infrared light is used to photograph the lens. Light in this range may also be used to determine light scattering by the lens.

Example 4

Using QLS/DLS to Determine Lenticular Protein Aggregate Size

DLS is used to ascertain the size of a lenticular protein aggregate. Using the fiber-optic probe described herein, focused light is transmitted from one optical fiber through a lens and onto an ocular lens. The focused light, scattered by the lenticular aggregates, is collected via a second lens, and passed along a second optical fiber. This light is detected by a photo diode array (such as a photo multiplier tube, or an avalanche photo diode detector) as the signal. The signal is extracted from the noise by passage through a digital correlator, yielding a decaying time autocorrelation function (TCF) which is plotted against the delay time. The decay rate of these data, determined from the best functional fit of the data, can be used to calculate the translational diffusion coefficient using equation 1, where $\Gamma$ is the decay rate, $D_t$ is the translation diffusion coefficient and q is the scattering vector.

$$\gamma = D_t q^2 \quad (1)$$

The scattering vector can be determined by equation 2, where q is the scattering vector, n is the refraction index, $\lambda$ is the wavelength of the scattered light, and $\Theta$ is the scattering angle.

$$q = \frac{4n\Pi}{\lambda} \sin\left(\frac{\Theta}{2}\right) \quad (2)$$

The scattering angle may be from about 0 degrees to about 180 degrees, preferably greater than 90 degrees to optimize back scattering. The size of the scattering particles varies with the angle measured. More preferably, the scattering angle is in a range of 90 to 178 degrees. Once the translation diffusion coefficient ($D_t$) is determined it can be used to calculate the hydrodynamic radius ($R_H$) of the protein using equation (3), where K is Boltzman's constant, T is absolute temperature of the suspending medium, and $\eta$ is the viscosity of the suspending medium.

$$D_t = \frac{KT}{6\eta\Pi R_H} \quad (3)$$

A viscosity value of ~0.69 Boise and a refractive index of ~1.333 are used in the above calculations for mouse lens. In a diagnostic technique, the values for viscosity and refractive index are relative and cancel out when comparing a healthy patient to a patient suspected or at risk of having an amyloidogenic disorder.

Figure 7A:
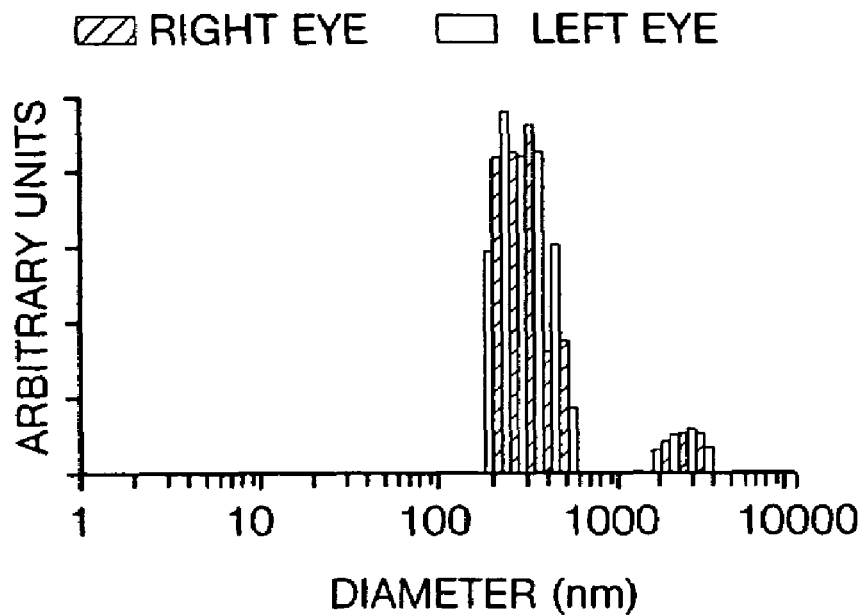
FIG. 7a is a QLS data graph depicting lens protein size distribution in the right eye (cross-hatched) and in the left eye (open) of control mice.
Figure 7B:
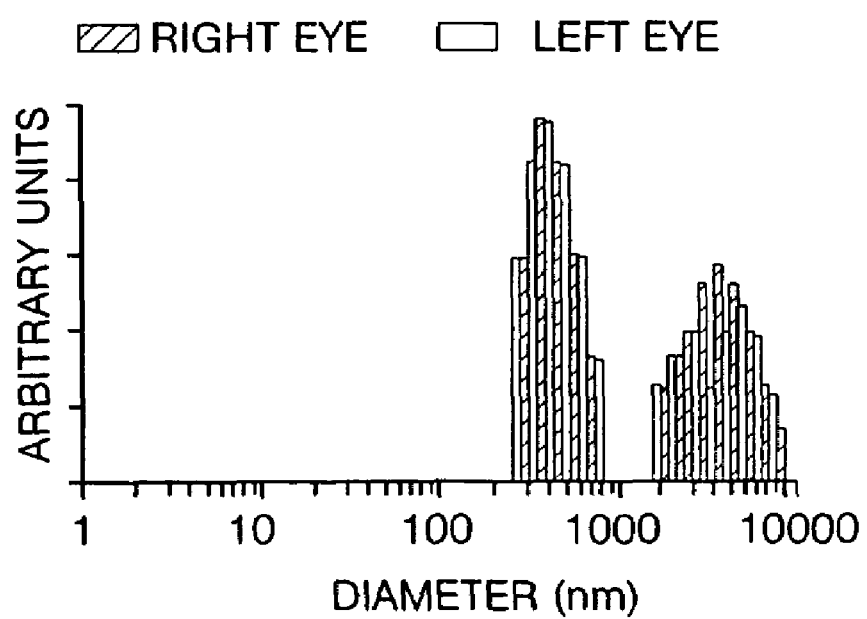
FIG. 7b is a QLS data graph depicting lens protein size distribution in the right eye (cross-hatched) and in the left eye (open) of transgenic mice Tg2576.

FIGS. 4, 5, 6a-b, and 7a-b show the results of QLS/DLS measurements of ocular lens tissue. FIG. 7a-b depict data using an art-recognized animal model for human AD, the transgenic Tg2576 mouse.

Example 5

Raman Scattering

Laser Raman spectroscopy is a powerful structural biochemistry technique which can safely provide information about regional lens hydration status (3417 cm−1), the lens water:protein ratio (expressed as Raman intensity ratio at 3417 cm−1:2936 cm−1), oxidation state of lens thiols, and the hydrogen bond microenvironment of the aromatic amino acid residues tryptophan (bands at 881 and 760 cm−1) and tyrosine (doublet near 840 cm−1). All of these factors are altered during cataractogenesis. Changes in the hydrogen-bonding microenvironment of tyrosine residues are particularly intriguing since dityrosine formation may be an important factor in Aβ aggregation. The instrument operating in the Raman spectroscopy mode is also used to detect and quantitate specific Aβ-lens protein associated Raman signature signals. For example, since Aβ has a high affinity for redox-active metal ions. Such interactions with these metals are involved in Aβ-lens protein aggregation. The Raman spectra is used in the 1750-720 cm−1 interval to detect Aβ-metal coordination and related phenomena (Suzuki et al., 2001, Biochem. Biophys. Res. Commun. 285: 991-996; Miura et al., 2000, Biochemistry 39:7024-7031; and Miura et al., 1999, Biochemistry 38: 11560-11569).

The fiber-optic probe is also used in a Raman scattering, or related Raman methodology mode. In laser Raman spectroscopy, a monochromatic laser light is directed onto a particular target material to be tested. For example, the bean is directed to the supranuclear region of the lens. A detection system then detects light returning, or scattered, from the target. The majority of the light returning from the material is scattered elastically at the same wavelength of the original projected laser light (Rayleigh scattering). A subset of the light returning from the material is scattered inelastically at a wavelength different from that of the original projected laser light in a manner known as Raman scattering. Raman scattered light is then separated from Rayleigh scattered light with the use of filters, optical gratings, prisms, and other wavelength selection techniques.

The energy difference between Raman and Rayleigh scattered light is related to the vibrational, rotational, or liberational states, or mixtures thereof, of various molecules in the material being evaluated. Each of the peaks in the resulting Raman spectrum corresponds to a particular Raman active vibration of a molecule or a component thereof. The Raman energy shift is independent of the wavelength of the directed laser light. The energy difference corresponding to the elastically and inelastically scattered light for a particular material remains constant for that material.

The data from Raman scattering is used to locate, identify and quantitate concentrations of a material. For example, the Raman fingerprint of an Aβ aggregate is different from that of an aggregate associated with an age-related nuclear cataract by virtue of i) signal localization within the lens (supranuclear/cortical versus nuclear), and ii) Aβ-lens protein and Aβ-metal interaction (and interactions between Aβ, other lens proteins, and metals).

Laser Raman spectroscopy is a powerful structural biochemistry technique which can safely provide information about regional lens hydration status ($3417\ cm^{-1}$), the lens water:protein ratio (expressed as Raman intensity ratio at $3417\ cm^{-1}:2936\ cm^{-1}$), oxidation state of lens thiols, and the hydrogen bond microenvironment of the aromatic amino acid residues tryptophan (bands at 881 and 760 $cm^{-1}$) and tyrosine (doublet near 840 cm−1). All of these factors are altered during cataractogenesis. Changes in the hydrogen-bonding microenvironment of tyrosine residues are particularly intriguing since dityrosine formation may be an important factor in Aβ aggregation. These signals associated with general cataractogenic phenomena are not specific for Aβ accumulation, but the presence of this process in the supranuclear/cortical region of the lens is consistent with the cumulative effects of Aβ accumulation and hence provide information about the presence or progression of AD. Raman spectroscopy mode is also used to detect and quantitate specific Aβ-lens protein associated Raman signature signals. For example, since Aβ has a high affinity for redox-active metal ions and interactions with these metals are involved in Aβ-lens protein aggregation, the Raman spectra in the 1750-720 cm−1 interval is used to detect Aβ-metal coordination and related phenomena (Suzuki et al., 2001, Biochem. Biophys. Res. Commun. 285: 991-996; Miura et al., 2000, Biochemistry 39:7024-7031; and Miura et al., 1999, Biochemistry 38: 11560-11569).

The absolute intensities of the resulting Raman peaks are directly related to the concentration of the Raman-active molecules in the material. The fingerprints are characterized by distinct spectral positions, signal strengths, and spectral widths. For example, a low power laser light in the range of 450-550 nm or is directed to the target region of the eye. Scattered light is optionally routed to a spectrally selective system, which selects only the Raman scattered light and rejects the Rayleigh scattered light to allow analysis of Raman signals absent interference from Rayleigh signals. Methods and devices for spectrally selecting scattered light are known in the art, e.g., grating monochromators, holographic filters, prisms, dielectrics, or combinations thereof.

A filter may be placed on both monomode optical fibers to allow only one frequency of light to be emitted or detected. The detected light is converted using a digital correlator into a spectrum that serves as a signature to detect protein aggregation. Interatomic vibration frequencies are recognized and assigned to specific protein aggregations. Using the techniques of Raman scattering, or related Raman methodology, the protein composition of an ocular aggregate is identified. An emission signature or Raman spectra, which indicates the presence of an Aβ aggregate, an Aβ-αB crystallin aggregate, a Aβ-αA crystallin aggregate, Aβ-β crystallin aggregate, or a Aβ-γ crystallin aggregate indicates a diagnosis of Alzheimer's Disease, or a predisposition to developing the disease or an amyloid disorder.

Example 6

In Vivo Determinations Using AD Mice

Tg2576 APPswed transgenic (Tg+) mice represent an art-recognized standard model for human AD. These mice express the amyloidogenic human "Swedish" double mutant APPswed (Alzheimers Precursor Proteins-swed), over express human Aβ, and develop cerebral neuropathology characteristic of human AD.

High molecular weight protein aggregation was detected in mice using the detection device shown in FIGS. 3c-d. An anesthesia unit connected to an anesthesia machine supplied a sufficient amount of halothane to anesthetize normal control mice or Tg2576 APPswed transgenic mice. The DLS probe was connected to a computer controlled motorized actuator to bring the lens housing into close proximity with a given mouse's eye. A laser source and photo detector encased together provided light emission to and detection from the DLS probe. Visible light of 665 nm wavelength from a laser diode was focused into a spot (20 μm diameter) inside a mouse's eye targeting the ocular lens. The detected signal was processed via a digital correlator to yield a time autocorrelation function (TCF). For dilute dispersions of spherical particles, the slope of the TCF provides a quick and accurate determination of the particles' translation diffusion coefficient. This may be related to the particles' size via a Stokes-Einstein equation provided that the viscosity of the suspending fluid, its temperature, and its refractive index are known. These parameters for mice lens are 0.6915 η(cp), 37° C., and 1.332, respectively.

Brownian motion of protein crystallin macromolecules inside the transgenic mice lens were monitored. As shown by the graphs of FIGS. 7a-b, there is a significant change in the size distribution of protein crystallins in the transgenic mice relative to its normal, or controlled, counterpart. FIG. 7a depicts the relative distribution of protein as a function of its globular diameter in healthy, control mice. Note that abscissae are plotted along a logarithmic (base 10) x-axis. This graph shows two clustered distributions of proteins: a major cluster centered around 400 nm and a less populated distribution centered around 3,000 nm. The distribution indicates that the bulk of protein molecules present in either left or right mouse eye lens have diameters less than 1000 nm with an average diameter value slightly greater than about 400 nm.

In contrast, FIG. 7b depicts the relative distribution of protein as a function of its globular diameter in Tg2576 APPswed transgenic mice. Note that abscissae are plotted along a logarithmic (base 10) x-axis. This graph also shows two clustered distributions of proteins, however, each cluster is shifted to the right relative to the clusters of FIG. 7a. Unlike the clusters of FIG. 7a, the clusters of FIG. 7b represent approximately equal populations. The left-most cluster is centered around 500 nm whereas the cluster on the right side is centered about 4000 nm. Hence, the average diameter of light scattering lenticular proteins in Tg2576 mice is roughly 2250 nm. The greater average diameter for lenticular protein accounts for the cloudy, cataractous lenses in Tg2576 mice. Note the shift in size distribution to higher values in the transgenic animal (FIG. 7b). This data was generated by non-invasive DLS measurements in halothane-anesthetized mice.

This DLS technique was used to document dense bilateral cataracts in Tg2576 APPswed transgenic mice as early as 10 months of age. At so early a stage, cerebral $hA\beta_{1-42}$ is just beginning to accumulate. Moreover, this technique was used to detect protein aggregation in Tg+ mice before a cataract was clinically present.

Example 6

Detection of Amyloidogenic Disorders in Human and Veterinary Patients

DLS and/or Raman scattering techniques to diagnose AD or other amyloidogenic disorders are easily carried out in a doctor's office, clinic or hospital setting. The methods are useful to assess patients for AD or related disorders including: AD, Familial AD, Sporadic AD, Creutzfeld-Jakob disease, variant Creutzfeld-Jakob disease, spongiform encephalopathies, Prion diseases (including scrapie, bovine spongiform encephalopathy, and other veterinary prionopathies), Parkinson's disease, Huntington's disease (and trinucleotide repeat diseases), amyotrophic lateral sclerosis, Down's Syndrome (Trisomy 21), Pick's Disease (Frontotemporal Dementia), Lewy Body Disease, neurodegeneration with brain iron accumulation (Hallervorden-Spatz Disease), synucleinopathies (including Parkinson's disease, multiple system atrophy, dementia with Lewy Bodies, and others), neuronal intranuclear inclusion disease, tauopathies (including progressive supranuclear palsy, Pick's disease, corticobasal degeneration, hereditary frontotemporal dementia [with or without parkisonism], Guam amyotrophic lateral sclerosis/parkinsonism dementia complex). These disorders may occur alone or in various combinations. Patients to be tested include those suspected of suffering from such disorders or who are at risk of developing such disorders. For example, patients with a family history of AD or other risk factors such as advanced age are tested using the techniques described herein.

The operator uses an instrument in the DLS and/or Raman modes to non-invasively and accurately ascertain the nature of protein aggregation in one or both eyes. The light is directed to target the ocular lens. However, since the amyloid proteins are also expressed in the cornea and elsewhere in the eye, other structures such as the cornea, the vitreous or aqueous humor, or other ocular constituents and components are targeted. The output from the device is a series of numbers which may be composited using the assistance of a computer. The number(s) are either within a normal range or outside a normal range and are compared to normed population data using this instrument in diseased and normal patient populations. This number or series of numbers is compared to prior measurements using this or similar devices and is assessed within the context of other clinical information. The use of this device is thus of aid in the diagnosis, prognosis, and monitoring of AD and related disorders. This information is useful to the patient, the patient's family, the assessing clinician, and other care providers, to determine future therapeutic strategies. The use of the device is also helpful in the staging of disease (e.g., pre-clinical, early, middle, late, etc.).

The methods and instrumentation is useful for monitoring the effectiveness of various treatments for AD and related disorders. For example, a decrease in the amount or a decline in the rate of formation of Aβ itself or Aβ-associated aggregates in eye tissue over time indicates improvement of AD or a related condition, e.g., as a result of successful therapeutic intervention.

All publications, patents and patent applications cited herein are fully incorporated by reference into the disclosure. Other embodiments are with the following claims.

What is claimed is:

1. A method of monitoring the effectiveness of a therapeutic intervention in a person suffering from or at risk for developing an amyloidogenic disorder, the method comprising
    detecting a polypeptide aggregate in a supranuclear or deep cortical region of an ocular lens, wherein said polypeptide aggregate comprises an amyloid protein selected from the group consisting of β-amyloid precursor protein (APP), Aβ, Aβ$_{1-42}$, prion protein, α-synuclein, and fragments thereof and wherein said polypeptide aggregate is detected using an ophthalmic instrument sensitive to light scattering; and
    monitoring the amount, the rate, or both the amount and the rate of aggregation over time;
wherein a decrease in the amount, the rate, or both the amount and rate of protein aggregation over time following therapeutic intervention indicates that the therapeutic intervention has clinical benefit.

2. The method of claim 1, wherein said polypeptide aggregate is detected by slit lamp examination.

3. The method of claim 1, wherein said polypeptide aggregate is detected by Scheimpflug optics.

4. The method of claim 3, wherein said amyloidogenic disorder is selected from the group consisting of Alzheimer's Disease (AD), Familial AD, Sporadic AD, Creutzfeld-Jakob disease, variant Creutzfeld-Jakob disease, spongiform encephalopathies, a Prion disease, Parkinson's disease, Huntington's disease (and trinucleotide repeat diseases), amyotrophic lateral sclerosis, Down's Syndrome (Trisomy 21), Pick's Disease (Frontotemporal Dementia), Lewy Body Disease, Hallervorden-Spatz Disease, a synucleinopathy, neuronal intranuclear inclusion disease, a tauopathy, Pick's disease, corticobasal degeneration, hereditary frontotemporal dementia, and Guam amyotrophic lateral sclerosis/parkinsonism dementia complex.

5. The method of claim 1, wherein said polypeptide aggregate is detected in a supranuclear region of said lens.

6. The method of claim 1, wherein said polypeptide aggregate is detected in a deep cortical region of said lens.

7. The method of claim 1, wherein said amyloidogenic disorder is Alzheimer's Disease.

8. The method of claim 1, wherein said polypeptide aggregate comprises an amyloid protein.

9. The method of claim 1, wherein said amyloid protein is β-amyloid precursor protein (APP).

10. The method of claim 1, wherein said polypeptide aggregate comprises a prion protein or fragment thereof.

11. The method of claim 1, wherein said polypeptide aggregate comprises α-synuclein.

12. The method of claim 1, wherein said amyloid protein is Aβ or a fragment thereof.

13. The method of claim 1, wherein said amyloid protein is Aβ$_{1-42}$.

14. The method of claim 1, wherein said polypeptide aggregate further comprises an ocular crystallin protein.

15. The method of claim 14, wherein said crystallin protein is selected from the group consisting of an α crystallin, β crystallin, and γ crystallin.

16. The method of claim 1, wherein said aggregate is detected by quasi-elastic light scattering.

17. The method of claim 1, wherein said polypeptide aggregate is detected by a Raman spectroscopic technique.

18. The method of claim 1, wherein said polypeptide aggregate is localized in a cytosol of an lens cortical fiber cell.

19. The method of claim 1, wherein said polypeptide aggregate is detected by light scattering.

20. The method of claim 1, wherein said polypeptide aggregate is detected by dynamic light scattering.

21. The method of claim 1, wherein said polypeptide aggregate is detected by static light scattering.

* * * * *

UNITED STATES PATENT AND TRADEMARK OFFICE
CERTIFICATE OF CORRECTION

| | | |
|---|---|---|
| PATENT NO. | : 7,653,428 B2 | Page 1 of 1 |
| APPLICATION NO. | : 11/511916 | |
| DATED | : January 26, 2010 | |
| INVENTOR(S) | : Goldstein et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 624 days.

Signed and Sealed this
Twenty-second Day of March, 2011

David J. Kappos
*Director of the United States Patent and Trademark Office*